US011459619B2

(12) United States Patent
Astatke et al.

(10) Patent No.: US 11,459,619 B2
(45) Date of Patent: Oct. 4, 2022

(54) HANDHELD NUCLEIC ACID-BASED ASSAY FOR RAPID IDENTIFICATION

(71) Applicant: The Johns Hopkins University, Balitmore, MD (US)

(72) Inventors: Mekbib Astatke, Gaithersburg, MD (US); Amy L. Connolly, Ijamsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 634 days.

(21) Appl. No.: 16/404,695

(22) Filed: May 6, 2019

(65) Prior Publication Data
US 2020/0040408 A1 Feb. 6, 2020

Related U.S. Application Data

(63) Continuation-in-part of application No. 15/017,683, filed on Feb. 8, 2016, now abandoned.

(51) Int. Cl.
C12M 1/34 (2006.01)
C12Q 1/6888 (2018.01)
C12Q 1/6865 (2018.01)

(52) U.S. Cl.
CPC ......... *C12Q 1/6888* (2013.01); *C12Q 1/6865* (2013.01)

(58) Field of Classification Search
USPC .............. 435/6.1, 6.11, 6.12, 7.1, 91.1, 91.2, 435/91.51, 287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 6,171,854 B1 | 1/2001 | Galler et al. |
| 6,589,531 B1 | 7/2003 | Andino-Pavlovsky et al. |
| 7,285,835 B2 | 10/2007 | Rizzo et al. |
| 7,312,036 B2 | 12/2007 | Sampath et al. |
| 7,699,979 B2 | 4/2010 | Li et al. |
| 8,124,592 B2 | 2/2012 | Nabel et al. |
| 8,715,694 B2 | 5/2014 | Apt et al. |
| 8,735,369 B2 | 5/2014 | Bavari et al. |
| 2004/0229221 A1 | 11/2004 | Schon |
| 2006/0223122 A1 | 10/2006 | Fogo et al. |
| 2006/0223197 A1 | 10/2006 | Vielsack |
| 2006/0234234 A1 | 10/2006 | Van Dongen et al. |
| 2006/0246453 A1 | 11/2006 | Kato et al. |
| 2010/0291144 A1 | 11/2010 | Ramanathan et al. |
| 2012/0025150 A1 | 2/2012 | Hersam et al. |
| 2012/0219576 A1 | 8/2012 | Branco et al. |

(Continued)

OTHER PUBLICATIONS

"List of sequenced bacterial genomes", Wikipedia.com; accessed Jan. 24, 2014, pp. 1-57.

(Continued)

*Primary Examiner* — Frank W Lu
(74) *Attorney, Agent, or Firm* — Todd R. Farnsworth

(57) ABSTRACT

A method for identifying a predefined target organism includes extracting a nucleic acid from a sample to form an extracted nucleic acid, amplifying the extracted nucleic acid to form a nucleic acid amplicon, tagging the nucleic acid amplicon with a capture probe and a detector partner to form a detector partner-nucleic acid amplicon-capture probe complex, and performing a detection assay on the detector partner-nucleic acid amplicon-capture probe complex to identify whether the predefined target organism is present in the sample.

17 Claims, 17 Drawing Sheets

Specification includes a Sequence Listing.

(56) References Cited

U.S. PATENT DOCUMENTS

| | | |
|---|---|---|
| 2013/0035248 A1 | 2/2013 | Icenhour |
| 2013/0040344 A1 | 2/2013 | Ju |
| 2013/0040843 A1 | 2/2013 | Von Toerne et al. |
| 2013/0040847 A1 | 2/2013 | Thrippleton et al. |
| 2013/0089558 A1 | 4/2013 | Tangy et al. |

OTHER PUBLICATIONS

L. Roewer, "DNA Fingerprinting in Forensics: Past, Present, Future", Investigative Genetics 2013; 4:22.

S. Reinholt et al., "Isolation and Amplification of mRNA within a Simple Microfluidic Lab on a Chip", NIH Public Access, Author Manuscript, Analytical Chemistry, Jan. 7, 2014, 86(1): 849-856.

M. Anissimov, "How Many Species of Bacteria Are There?", wiseGeek.com, accessed Jan. 21, 2014, available at wisegeek.com/how-many-species-of-bacteria-are-there.htm, pp. 1-7.

Y. Luo et al., "Genotyping Mitochondrial DNA Single Nucleotide Polymorphisms by PCR Ligase Detection Reactions", Clinical Chem Lab Med 2010, 48(4):475-483.

"Custom Antibody Services", Precision Antibody, available at http://precisionantibody.com/custom-anti-body-services/?gclid=CM-br6jx-LwCFTDxOgod1 . . . , accessed Mar. 4, 2014, pp. 1-2.

M. Hammer, "Human Hybrids", Scientific American, May 2013, pp. 66-71.

"Ebola Virus", Wikipedia, available at https://en.wikipedia.org/wiki/Ebola_virus, accessed Jan. 29, 2019, pp. 1-10.

S. Begley, "Psst, the human genome was never completely sequenced. Some scientists say it should be . . . ", STAT, available at https://www.statnews.com/2017/06/20/human-genome-not-fully-sequenced/, accessed Jun. 20, 2017, pp. 1-8.

R. Alaeddini, "Forensic Implications of PCR Inhibition—A Review", Elsevier, Forensic Science International, Genetics 6, 2012, pp. 297-305.

N. Ali et al., "Current Nucleic Acid Extraction Methods and Their Implications to Point-of-Care Diagnostics", Hindawi, BioMed Research International, vol. 2017, Article ID 9306564, pp. 1-13.

S. Boguslawski et al., "Characterization of Monoclonal Antibody to DNA—RNA and its Application to Immunodetection of Hybrids", Elsevier, Journal of Immunological Methods, 89, 1986, pp. 123-130.

J. Compton, "Nucleic Acid Sequence-Based Amplification", Nature, Volumbe 350, Mar. 7, 1991, pp. 91-92.

B. Deiman et al., "Characteristics and Applications of Nucleic Acid Sequence-Based Amplifications (NASBA)", Molecular Biology Review, vol. 20, 2002, pp. 163-179.

C. Drosten et al., "Rapid Detection and Quantification of RNA of Ebola and Marburg Viruses, Lassa Virus, Crimean-Congo Hemorrhagic Fever Virus, Rift Valley Fever Virus, Dengue Virus, and Yellow Fever Virus by Real-Time Reverse Transcription-PCR", Journal of Clinical Microbiology, vol. 40, No. 7, Jul. 2002, pp. 2323-2330.

E. Fahy et al., "Self-Sustained Sequence Replication (3SR): An Isothermal Transcription-based Amplification System Alternative to PCR", Cold Spring Harbor Laboratory Press, PCR Methods and Applications, 1991, vol. 1(1), pp. 25-33.

X. Fang et al., "Predicting Viruses Accurately by a Multiplex Microfluidic Loop-Mediated Isothermal Amplification Chip", Analytical Chemistry Letter, ACS Publications, 2010, 83:690-695.

J. Goldmeyer et al., "Identification of *Staphylococcus aureus* and Determination of Methicillin Resistance Directly from Positive Blood Cultures by Isothermal Amplification and a Disposable Detection Device", Journal of Clinical Microbiology, vol. 46, No. 4, Apr. 2008, pp. 1534-1536.

K. Gracias et al., "Nucleic Acid Sequence-Based Amplification (NASBA) in Molecular Bacteriology: A Procedural Guide", Journal of Rapid Methods & Automation in Microbiology, 15, 2007, pp. 295-309.

D. Graves, "Powerful Tools for Genetic Analysis Come of Age", Elsevier Science, trends in Biotechnology, vol. 17, Issue 3, Mar. 1999, pp. 127-134.

A. Kitts, et al., "The Database of Short Genetic Variation (dbSNP)", The NCBI Handbook (Internet), 2nd edition, Bethesda, MD, National Center for Biotechnology Information (2014), pp. 1-41.

M. Mathiyazhakan et al., "A Concise Review of Gold Nanoparticles-Based Photo-Responsive Liposomes for Controlled Drug Delivery," Nano-Micro Lett. (2018) 10:10, published on-line in Oct. 2017.

C. Moore, "Point-of Care Tests for Infection Control: Should Rapid Testing be in the Laboratory or at the Front Line?", Elsevier, Journal of Hospital Infection 85 (2013), available online at sciencedirect. com, pp. 1-7.

A. Niemz et al., "Point-of-Care Nucleic Acid Testing for Infectious Diseases", NIH Public Access, Author Manuscript, Trends Biotechnology, May 2011, 29(5); 240-250.

D. Phillips et al., "The Sub-Nanomolar Binding of DNA—RNA Hybrids by the Single Chain Fv Fragement of Antibody S9.6," J Mol Recognit. (2013) 26(8): 376-381.

B. Rohrman et al., "A Lateral Flow Assay for Quantitative Detection of Amplified HIV-1 RNA", PLOS ONE, Sep. 2012, vol. 7, Issue 9, 1-8.

J. Sun et al., "Point-of-Care Biochemical Assays Using Gold Nanoparticle-Implemented Microfluidics," Chem. Soc. Rev. (2014) 43, 6239-6253.

S. Wu et al., "Detection of Dengue Viral RNA Using a Nucleic Acid Sequence-Based Amplification Assay", Journal of Clinical Microbiology, Aug. 2001, vol. 39, No. 8, pp. 2794-2798.

L. Yan et al., "Isothermal Amplified Detection of DNA and RNA", Molecular BioSystems, (2014) 10, 970-1003.

R. Peeling et al., "Emerging technologies in point-of-care molecular diagnostics for resource-limited settings, Expert Review of Molecular Diagnostics," (2014) 14:5, 525-534.

Flowchart for NASBA Coupled with DNA Probe Tagging Using as an Example Targeting Ebola Virus L gene _Ebola Virus L gene (AF086833)_
GGGAGA
13321 SEQ ID NO: 5

13321 SEQ ID NO: 5

→ NASBA Probe T7 Probe Hybridization
Step-One RT catalyzed Synthesis

SEQ ID NO: 6

→ 1st strand Synthesis
& reverse Probe hybridization

→ 2nd strand Synthesis

SEQ ID NO: 7

FIG 15A

SEQUENCE LISTING

<160> NUMBER OF SEQ ID NOS: 8

<210> SEQ ID NO 1
<211> LENGTH: 480
<212> TYPE: DNA
<213> ORGANISM: Ebola Virus

<400> SEQUENCE: 1

```
ctactaccac aatatcggaa cttttctttc tcattgaaag agaaagagtt gaatgtaggt      60
agaaccttcg gaaaattgcc ttatccgact cgcaatgttc aaacactttg tgaagctctg     120
ttagctgatg gtcttgctaa agcatttcct agcaatatga tggtagttac ggaacgtgag     180
caaaaagaaa gcttattgca tcaagcatca tggcaccaca caagtgatga ttttggtgaa     240
catgccacag ttagagggag tagctttgta actgatttag agaaatacaa tcttgcattt     300
agatatgagt ttacagcacc ttttatagaa tattgcaacc gttgctatgg tgttaagaat     360 gttttttaatt ggatgcatta tacaatccca cagtgttata tgcatgtcag tgattattat     420
aatccaccac ataacctcac actggagaat cgagacaacc ccccgaagg gcctagttca      480
```

<210> SEQ ID NO 2
<211> LENGTH: 342
<212> TYPE: DNA
<213> ORGANISM: Lassa Virus

<400> SEQUENCE: 2

```
attatataat gatgactgtt gttctttgtg caggagagag gcatggtcat attgagtgtc      60
tccatgttta gttccagagt ctgaagctca taaaccccctt tataaagact ggttgtgcaa    120
gacctaccac acaacaggag gaaagtgacc aaaccaacaa ggccacacgt tgcaaaattg    180
tacagacctt tcagcactgc tagtacagac agtgcaatga gaacaatgtt catcacctct    240
tctattacat gaggcacttc ctggaagaat gtcactattt gtcccatttt aaataggaca    300
cttgaattgc gcaaccaaaa atgcctagga tccccggtgc gc                       342
```

<210> SEQ ID NO 3
<211> LENGTH: 300
<212> TYPE: DNA
<213> ORGANISM: Dengue Virus

<400> SEQUENCE: 3

```
tcaggccgaa agccacggtt tgagcaaacc gtgctgcctg tagcttcatc gtggggatgt      60
aaaaacctgg gaggctgcaa cccatggaag ctgtacgcat ggggtagcag actagtggtt    120
agaggagacc cctcccaaaa cataacgcag cagcggggcc caacaccagg ggaagctgta    180
tcctggtggt aaggactaga ggttagagga dacccccggc ataacaataa acagcatatt    240
gacgctggga gagaccagag atcctgctgt ctctacagca tcattccagg cacagaacgc    300
```

<210> SEQ ID NO 4
<211> LENGTH: 180
<212> TYPE: DNA
<213> ORGANISM: Yellow Fever Virus

<400> SEQUENCE: 4

```
agtaaatcct gtgtgctaat tgaggtgcat tggtctgcaa atcgagttgc taggcaataa      60
acacatttgg attaatttta atcgttcgtt gagcgattag cagagaactg accagaacat    120
gtctggtcgt aaagctcagg gaaaaaccct gggcgtcaat atggtacgac gaggagttcg    180
```

```
<210> SEQ ID NO 5
<211> LENGTH: 360
<212> TYPE: DNA
<213> ORGANISM: Ebola Virus

<400> SEQUENCE: 5
ttagctgatg gtcttgctaa agcatttcct agcaatatga tggtagttac ggaacgtgag      60
caaaaagaaa gcttattgca tcaagcatca tggcaccaca caagtgatga ttttggtgaa     120
catgccacag ttagagggag tagctttgta actgatttag agaaatacaa tcttgcattt     180
agatatgagt ttacagcacc ttttatagaa tattgcaacc gttgctatgg tgttaagaat     240
gtttttaatt ggatgcatta tacaatccca cagtgttata tgcatgtcag tgattattat     300
aatccaccac ataacctcac actggagaat cgagacaacc ccccgaagg gcctagttca      360

<210> SEQ ID NO 6
<211> LENGTH: 511
<212> TYPE: DNA
<213> ORGANISM: Ebola Virus

<400> SEQUENCE: 6
ccctctgatg atggtgttat agccttgaaa agaaagagta actttctctt tctcaactta      60
catccatctt ggaagccttt taacggaata ggctgagcgt acaagtttg tgaaacactt      120 cgagacaatc gactaccaga acgatttcgt aaaggatcgt tatactacca tcaatgcctt     180
gcactcgttt ttcttcgaa taacgtagtt cgtagtaccg tggtgtgttc actactaaaa      240
ccacttgtac ggtgtcaatc tccctcatcg aaacattgac taaatctctt tatgttagaa     300
cgtaaatcta tactcaaatg tcgtggaaaa tatcttataa cgttggcaac gataccacaa     360
ttcttacaaa aattaaccta cgtaatatgt tagggtgtca caatatacgt acagtcacta     420
ataatattag gtggtgtatt ggagtgtgac ctcttagctc tgttgggggg gcttcccgga     480
tcaagtggga tatcactcag cataatctta a                                    511

<210> SEQ ID NO 7
<211> LENGTH: 984
<212> TYPE: DNA
<213> ORGANISM: Ebola Virus

<400> SEQUENCE: 7
tatcggaact tttctttctc attgaaagag aaagagttga atgtaggtag aaccttcgga      60
aaattgcctt atccgactcg caatgttcaa acactttgtg aagctctgtt agctgatggt     120
ctatagcctt gaaagaaag agtaactttc tctttctcaa cttacatcca tcttggaagc     180
cttttaacgg aataggctga gcgttacaag tttgtgaaac acttcgagac aatcgactac     240
cagatgctaa agcatttcct agcaatatga tggtagttac ggaacgtgag caaaaagaaa     300
gcttattgca tcaagcatca tggcaccaca caagtgatga ttttggtgaa catgccacag     360
ttacgatttc gtaaaggatc gttatactac catcaatgcc ttgcactcgt ttttctttcg     420
aataacgtag ttcgtagtac cgtggtgtgt tcactactaa aaccacttgt acggtgtcaa     480
tcagggagta gctttgtaac tgatttagag aaatacaatc ttgcatttag atatgagttt     540
acagcacctt ttatagaata ttgcaaccgt tgctatggtt taagaatgt ttttaattgg     600 attccctcat cgaaacattg actaaatctc tttatgttag aacgtaaatc tatactcaaa     660
tgtcgtggaa atatcttat aacgttggca acgataccac aattcttaca aaaattaacc     720
tagcattata caatcccaca gtgttatatg catgtcagtg attattataa tccaccacat     780
```

```
aacctcacac tggagaatcg agacaacccc cccgaagggc ctagttcacc ctatagtgag      840
tcgtattaga attcgtaata tgttagggtg tcacaatata cgtacagtca ctaataatat      900
taggtggtgt attggagtgt gacctcttag ctctgttggg ggggcttccc ggatcaagtg      960
ggatatcact cagcataatc ttaa                                             984

<210> SEQ ID NO 8
<211> LENGTH: 468
<212> TYPE: DNA
<213> ORGANISM: Ebola Virus

<400> SEQUENCE: 8
atagccttga aagaaagag taactttctc tttctcaact tacatccatc ttggaagcct        60
tttaacggaa taggctgagc gttacaagtt tgtgaaacac ttcgagacaa tcgactacca     120
gaacgatttc gtaaaggatc gttatactac catcaatgcc ttgcactcgt ttttctttcg     180
aataacgtag ttcgtagtac cgtggtgtgt tcactactaa aaccacttgt acggtgtcaa     240
tctccctcat cgaaacattg actaaatctc tttatgttaa aacgtaaatc tatactcaaa     300
tgtcgtggaa aatatcttat aacgttggca acgataccac aattcttaca aaaattaacc     360 tacgtaaatat gttagggtgt cacaatatac gtacagtcac taataatatt aggtggtgta    420
ttggagtgtg acctcttagc tctgttgggg gggcttcccg gatcaagt                  468
```

HANDHELD NUCLEIC ACID-BASED ASSAY FOR RAPID IDENTIFICATION

CROSS REFERENCE TO RELATED APPLICATIONS

This application is a continuation-in-part of now abandoned U.S. application Ser. No. 15/017,683, filed Feb. 8, 2016.

TECHNICAL FIELD

Example embodiments relate generally to methods and devices for identifying target organisms and more particularly to methods and handheld devices for identifying biological agents (e.g., pathogens) and particular human individuals.

BACKGROUND

Rapid identification of biological agents (e.g., pathogens) is crucial during disease outbreaks. Moreover, rapid human identification for forensic applications is critical when solving crimes. However, current identification methods require transporting samples to laboratories to test in large machines or bringing these heavy machines to the scene. The available identification methods and devices do not allow identification of multiple biological agents with high sensitivity or specificity and further do not permit analysis of degraded DNA samples. As such, both identification of biological agents and human individuals in the field, although very important, are extremely difficult using existing technology. Most existing nucleic acid detection platforms require amplified product hybridization with an oligonucleotide probe on a solid surface that significantly limits target capture. In addition, it is difficult to develop a multiplex detection format employing oligonucleotide detector partners since each amplified target would require a unique detector identifier.

Therefore there at least remains a need in the art for a lightweight, portable, cost-effective device for identifying a target organism(s) and methods of operating thereof.

The ASCII sequence listing file titled "sequence," created Oct. 18, 2019, with a size of 5,653 bytes is hereby incorporated by reference in its entirety.

BRIEF SUMMARY

One or more example embodiments address one or more of the aforementioned problems. Certain example embodiments provide a method for identifying a predefined target organism. In accordance with certain embodiments, the method may comprise extracting a nucleic acid from a sample to form an extracted nucleic acid, amplifying the extracted nucleic acid to form a nucleic acid amplicon, tagging the nucleic acid amplicon to a capture probe and a detector partner to form a detector partner-nucleic acid amplicon-capture probe complex, and performing a detection assay on the detector partner-nucleic acid amplicon-capture probe complex to identify whether the target organism is present in the sample.

In another aspect, a handheld device for identifying a target organism is provided. The device may comprise a nucleic acid extraction portion, the nucleic acid extraction portion being configured to extract nucleic acid from a sample to form extracted nucleic acid; a nucleic acid amplification portion, the nucleic acid amplification portion being configured to amplify the extracted nucleic acid to form a nucleic acid amplicon; a tagging portion, the tagging portion being configured to hybridize the nucleic acid amplicon to a capture probe and a detector partner to form a detector partner-nucleic acid amplicon-capture probe complex; and a detection portion, the detection portion being configured to perform a detection assay on the detector partner-nucleic acid amplicon-capture probe complex.

BRIEF DESCRIPTION OF THE DRAWING(S)

Having thus described example embodiments in general terms, reference will now be made to the accompanying drawings, which are not necessarily drawn to scale, and wherein:

FIGS. 15A and 15B is an example flowchart illustrating nucleic acid sequence-based amplification coupled with DNA probe tagging according to an example embodiment.

DETAILED DESCRIPTION

Figure 1:
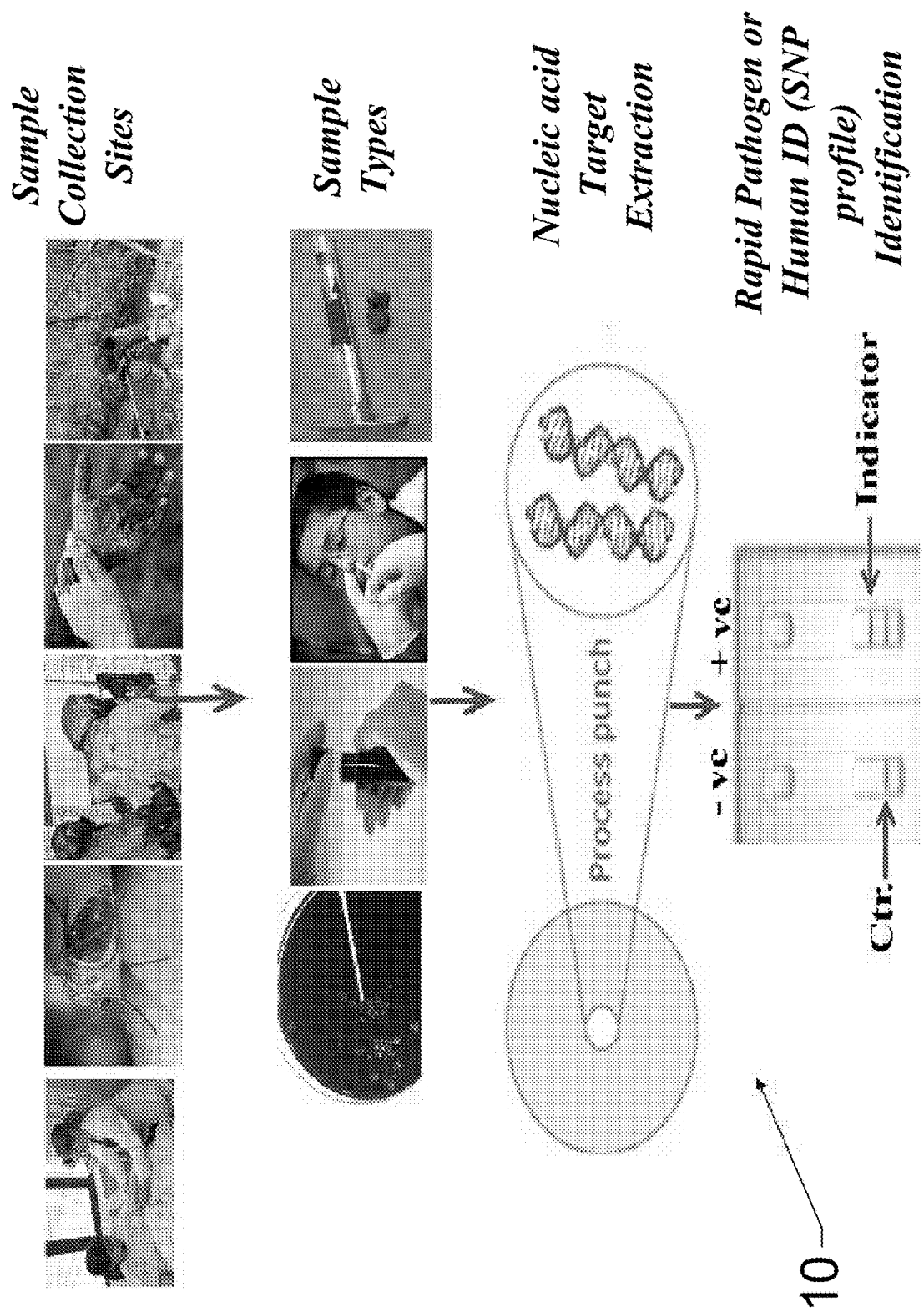
FIG. 1 illustrates an overview of a method for identifying a target organism according to an example embodiment.

Some example embodiments now will be described more fully hereinafter with reference to the accompanying drawings, in which some, but not all embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numeral refer to like elements throughout. As used in the specification, and in the appended claims, the singular forms "a", "an", "the", include plural referents unless the context clearly dictates otherwise. All references and documents referenced below are hereby incorporated herein in their entirety.

Certain example embodiments provide methods and devices for identifying predefined and previously identified target organisms. For instance, such methods and devices may provide, for example, a lightweight, cost-effective means of identifying, for instance, pathogens and/or individuals. For example, in an embodiment, the invention enables the direct linking of molecular based assay that targets and exponentially amplifies nucleic acid sequences with simple immunoassay detection platforms that are more suitable for portable detection formats. More specifically, in this embodiment the invention enables the selective amplification of genomic targets (using specific amplification probes) with established isothermal amplification methods such as Nucleic Acid Sequence-Based Amplification (NASBA) called process that entails a one-step RNA amplification that results in generating multiple copies of the complementary RNA strand (amplicon). The resultant amplicon is tagged with a DNA probe to form a DNA/RNA hybrid followed with the detection using a "Detector Partner", an antibody Ab) that selectively binds to DNA/RNA hybrids, in an immunoassay detection format. The isothermal amplification process, unlike polymerase chain reaction (PCR), can performed at a one temperature will not require large instrumentation and linked to an immunoassay detection format enables the development of portable sensor device. More specifically, the immunoassay detection format is a lateral flow (LF) detection format that enables chromatographic wicking of the tagged amplicon-Ab complex on a membrane to be detected and visualized at a specific position.

To be clear, since each pathogen carries unique genomic sequences, by targeting and amplifying these unique sections of sequences the identity of an organism in a sample can be ascertained. In similar vein, individuals carry unique specific variations at specific positions throughout the genome known as single nucleotide polymorphisms (SNPs) that can be assessed in order to determine attribution based on population genetics statistical analysis. For example, a detector partner that universally binds to all amplicons based on conformational motif may be employed regardless of amplicon sequence variations, and the respective amplicon may be captured at specific positions via a sequence specific capture probe labeled with a moiety that specifically binds to a pre-coated binding partner. This is important aspect of the invention in that a unique segment of pathogen genome can be targeted, generated using selective probes designed to only hybridize to the said pathogen sequence via Watson-Crick base pairing, to generate a resultant amplicon which then can bind to the detector partner. The universality of the detector partner to all amplicons enables it to be part of an automated detector platform, easily suitable to far-forward detection applications. The amplification mix, the mix that is obtained at the end of the amplification reaction step after the addition of the sample (with or without the target pathogen) to a reaction mixture that contains probe/s that hybridize to the target genome sequences, polymerase (catalyzes the probe extension reaction) and buffer components required for the amplification reactions.

In one embodiment, this is achieved using a partner that binds selectively to the amplicon, generated in the initial amplification reaction, based on unique conformational (tertiary) interactions that are not present in the reactants (e.g., primers). The partner can also be adsorbed onto a surface matrix to enable selective enrichment of the amplicon. Following an incubation step between an amplification mix and the coated surface, that ensures the binding of the amplicon to the surface via the interaction with the partner, the surface is washed successively to remove unbound reaction components. In one embodiment, the partner is an antibody raised against an epitope only present in the amplicon—for example an RNA/DNA hybrid which is generated from nucleic acid sequence based amplification (NASBA) based amplification and a hybridization step. The antibody is adsorbed on a surface (e.g., a 96 well polystyrene plate surface) via an established process for enzyme-linked immunosorbent assay (ELISA) format immunoassays. The example embodiments of the invention described herein significantly enhance the development of multiplex detection formats to enable the interrogation of a sample for the presence of multiple organisms or targets simultaneously. As such, for example, the methods and devices may permit the identification of pathogens and/or individuals at sample collection sites, thereby limiting the need to ship samples to laboratories and, as a result, providing rapid readouts, thereby permitting faster identification of pathogens and/or individuals in urgent situations (e.g., disease outbreak, criminal activity, etc.). For field forward applications, detection uses an adapted lateral flow (LF) based format where the antibody will be labeled with a reporter moiety such as a gold-nanoparticle. Most current commercial diagnostic tests suitable for far field settings are based on immuno-chromatographic LF platforms which are small, low weight, portable, and easy to use. As shown, for example, in Moore, "Point-of-care tests for infection control: should rapid testing be in the laboratory or at the front line?," Journal of Hospital Infection 85 (2013) 1-7, the contents of which are hereby incorporated by reference in their entirety. However, LF devices use antibody (Ab) or antigen identification tests that lack sensitivity and specificity and are rarely capable of multiplexing. On the other hand, molecular techniques that interrogate unique pathogen nucleic acid (NA) sequences, by amplifying target sequences via polymerase chain reaction (PCR), are extremely sensitive and specific for identifying biological agents. As shown in Rosanna W Peeling & Ruth McNerney (2014) Emerging technologies in point-of-care molecular diagnostics for resource-limited settings, Expert Review of Molecular Diagnostics, 14:5, 525-534, the contents of which are hereby incorporated by reference in their entirety. However, PCR requires complex instrumentation, limiting its use in austere environments. Recently, advancements in isothermal NA amplification techniques have opened the possibility for highly sensitive assays developments suitable for field-forward settings (as shown by Yan et. al., "Isothermal amplified detection of DNA and RNA," Molecular BioSystems, 2014, 10: 970-1003, the contents of which are hereby incorporated by reference in their entirety). However, these amplification technology formats employed to-date do not lend well for identification of multiple organisms concurrently in a sample of interest. The critical limitations include difficulty to: a) integrate and automate required steps, b) provide identification of all etiological agents of infections present in a sample, c) identify organisms in co-infections and/or where clinical indications of multiple organisms are indistinguishable etc. These technology gaps are especially difficult to overcome if the end-user is at site far removed from a laboratory facility and/or when urgent sample analysis is critical to the mission. In an embodiment of the present invention, the LF uses a membrane strip and at specific positions on the membrane strip the DNA/RNA hybrid will be bound via the interaction between a modification on the DNA probe and capture partner (e.g., biotin and streptavidin). When the NASBA process produces RNA, the DNA probe will form a DNA/RNA hybrid which will form a complex with the labeled Ab (with gold-nanoparticle) and which then can be visualized as a complex at the capture zone on the LF membrane. In one embodiment, the method steps include, for example:

| Assay Steps | Details |
|---|---|
| I (NA Extraction) | Pathogen nucleic acid (RNA target) extraction/enrichment technique compatible with the disposable prototype cartridge or sample collection tube |
| II (Amplification/ Tagging) | NASBA based isothermal amplification (41° C.) of target RNA using a combination of 3 enzymes: reverse transcriptase, T7 DNA polymerase and ribonuclease H (RNase H) followed with amplicon tagging probe that carries a unique moiety e.g., biotin |
| III (Anti-NA/ RNA Ab) | Formation of amplicon-tagged probe-detector partner complex (anti-DNA/RNA antibody-amplicon-tagging probe) |
| IV (Detection) | Capture of complex (step III) to a specific surface via an interaction between unique moiety on the tagging probe and a pre-coated capture partner (e.g., biotin-streptavidin) coated on each well. |

Although particular viruses, bacteria, and/or the like are frequently referenced throughout this disclosure, these particular biological agents serve only as exemplary embodiments, and, as such, this disclosure should not be limited to such biological agents, as other exemplary embodiments could be applicable to a wide variety of protein-based biological agents. Moreover, although single nucleotide polymorphisms (SNPs) are referenced in regard to human identification applications, SNPs may also be used in other applications including, for example, biological agent drug resistance analyses.

I. Definitions

As used herein, the terms "antibody" and "antibodies" comprise a glycoprotein substantially encoded by an immunoglobulin gene or immunoglobulin genes, or fragments thereof, which specifically recognize and bind foreign molecules called antigens. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. Fab fragments are the antigen-binding domains of an antibody molecule. Fab fragments can be prepared by papain digestions of whole antibodies. Fv fragments are the minimal fragment (~30 kDa) that still contains the whole antigen-binding site of a whole IgG antibody. Fv fragments are composed of both the variable heavy chain ($V_H$) and variable light chain ($V_L$) domains. This heterodimer, called Fv fragment (for fragment variable) is still capable of binding the antigen. The term "antibody," as used herein, also includes antibody fragments either produced by the modification of whole antibodies or those synthesized de novo using recombinant DNA methodologies, and further includes "humanized" antibodies made by now conventional techniques. In one embodiment the specific antibodies used to demonstrate proof-of concept was a monoclonal IgG that has been described by Boguslawski et al., "Characterization of monoclonal antibody to DNA.RNA and its application to immunodetection of hybrids" Journal of Immunological Methods, 89 (1986) 123-130; and Phillips, D. D., et al., "The sub-nanomolar binding of DNA-RNA hybrids by the single chain Fv fragment of antibody S9.6," J. Mol. Recognit. (2013) 26(8):376-381, the contents of which are hereby incorporated by reference in their entirety.

The term "hapten", as used herein, comprises a small molecule, not antigenic by itself, which can react with specific antibodies and elicit the formation of such antibodies when conjugated to a larger antigenic molecule, usually a protein, called in this context the carrier.

The terms "extracting", "extracted", and "extract", as used herein, refer to any compatible means of extracting nucleic acids as understood by one of ordinary skill in the art. Certain exemplary embodiments comprise RNA extraction or DNA extraction depending on the application of a given embodiment disclosed herein. RNA extraction, for example, refers to the purification of RNA from biological samples. This procedure is complicated by the ubiquitous presence of ribonuclease enzymes in cells and tissues, which can rapidly degrade RNA. Several methods are used in molecular biology to isolate RNA from samples, the most common of these is Guanidinium thiocyanate-phenol-chloroform extraction. The filter paper based lysis and elution method features high throughput capacity.

The term "lysing", "lysed", and "lyse", as used herein, refer to the breaking down of the membrane of a cell, often by viral, enzymatic, or osmotic mechanisms that compromise its integrity. Cell lysis may be used to break open cells and purify or further study their contents and may be affected by enzymes or detergents or other chaotropic agents.

The term "amplicon", as used herein, comprise a piece of DNA or RNA that is the source and/or product of natural or artificial amplification or replication events. There are known factors that can hinder nucleic acid amplification reactions such as the presence of environmental and clinical contaminants in the reaction mixture. Several approaches have been developed to neutralize inhibitors and improve amplification proficiencies such as: heat-soaked PCR, hot start PCR, chromatographic removal of inhibitors and extensive sample dilution. See, for example, Reza Alaeddini, "Forensic implications of PCR inhibition—A review," Forensic Science International: Genetics 6 (2012) 297-305, the contents of which are hereby incorporated by reference in their entirety. Amplicons in general are direct repeat (head-to-tail) or inverted repeat (head-to-head or tail-to-tail) genetic sequences, and can be either linear or circular in structure. The terms "amplifying", "amplified", "amplify", and "amplification", as used herein, refers to the production of one or more copies of a genetic fragment or target sequence, specifically the amplicon. As the product of an amplification reaction, amplicon is used interchangeably with common laboratory terms, such as PCR product.

The term "single nucleotide polymorphism (SNP)", as used herein, comprise variation in a single nucleotide which occurs at some specific position in the genome, where each variation is present to some appreciable degree within a population (e.g. >1%). For example, at a specific base position in the human genome, it may be that in most individuals the base C appears there; but in a minority of individuals, the base A appears at that position instead. There is an SNP at this specific base position, and the two possible nucleotide variations—C or A—are said to be alleles for this base position. Although in this example and most SNPs so far discovered there are only two different alleles, there are also triallelic SNPs in which three different base variations may coexist within a population. Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code. SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene. The genomic distribution of SNPs is not homogenous; SNPs occur in non-coding regions more frequently than in coding regions or, in general, where natural selection is acting and 'fixing' the allele (eliminating other variants) of the SNP that constitutes the most favorable genetic adaptation. Other factors, like genetic recombination and mutation rate, can also determine SNP density. There are variations between human populations, so a SNP allele that is common in one geographical or ethnic group may be much rarer in another. Within a population, SNPs can be assigned a minor allele frequency—the lowest allele frequency at a locus that is observed in a particular population. This is simply the lesser of the two allele frequencies for single-nucleotide polymorphisms.

The term "DNA strand displacement", as used herein, refers to the ability to displace downstream DNA encountered during synthesis. In strand-displacement replication, only one strand is replicated at once. This synthesis releases a single stranded DNA, which is in turn copied into double strand-DNA.

The terms "hybridizing", "hybridize", and "hybridized", as used herein, refers to a phenomenon in which single-stranded deoxyribonucleic acid (DNA) or ribonucleic acid (RNA) molecules anneal to complementary DNA or RNA. Though a double-stranded DNA sequence is generally stable under physiological conditions, changing these conditions in the laboratory (generally by raising the surrounding temperature) will cause the molecules to separate into single strands. These strands are complementary to each other but may also be complementary to other sequences present in their surroundings. Lowering the surrounding temperature allows the single-stranded molecules to anneal or "hybridize" to each other. DNA replication and transcription of DNA into RNA both rely upon nucleotide hybridization. The terms "tagging" and "tagged", as used herein, refer to the hybridization of an amplicon to a probe, such as a capture probe and/or a detector partner.

The term "capture probe", as used herein, comprises a nucleic acid sequence probe (e.g., oligomer) that contains a binding moiety (e.g., biotin, digoxigenin, etc.) to anchor the amplicon or detector partner-nucleic acid amplicon-complex to a specific surface following hybridization at a specific sequence region of a respective amplicon.

The term "detector partner", as used herein in the context of identifying a target biological agent, comprises an antibody labeled with a detector moiety (e.g., gold nanoparticle, fluorophore, etc.) that will bind to DNA/RNA hybrids and/or RNA structures, regardless of sequence compositions. The term "detector partner", as used herein in the context of human identification, comprises a nucleic acid sequence probe (e.g., oligomer) coated with a detector moiety (e.g., gold nanoparticle, fluorophore, etc.) that will selectively hybridize with a sequence region of a respective amplicon. For example, Graves, D. J, "Powerful tools for genetic analysis come of age," Trends in Biotechnology, Volume 17, Issue 3, 1 Mar. 1999, Pages 127-134, the contents of which are incorporated herein by reference in its entirety.

The term "detection assay", as used herein, comprises a biochemical test that measures the presence or concentration of a macromolecule in a solution through the use of an antibody. Immunoassays rely on the ability of an antibody to recognize and bind a specific macromolecule in what might be a complex mixture of macromolecules. In immunology the particular macromolecule bound by an antibody is referred to as an antigen and the area on an antigen to which the antibody binds is called an epitope. In some cases an immunoassay may use an antigen to detect for the presence of antibodies, which recognize that antigen, in a solution. In other words, in some immunoassays, the analyte may be an antibody rather than an antigen. In addition to the binding of an antibody to its antigen, the other key feature of all immunoassays is a means to produce a measurable signal in response to the binding. For example, the detection assay may comprise a two-site, noncompetitive immunoassay (i.e. a sandwich assay). Examples of sandwich assays may include, for instance, lateral flow assays, enzyme-linked immunosorbent assays (ELISAs) and/or the like.

The term "lateral flow assay", as used herein, comprises devices intended to detect the presence (or absence) of a target analyte in sample (matrix) without the need for specialized and costly equipment. The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these stripes, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the absorbent pad, which simply acts as a waste container.

The term "enzyme-linked immunosorbent assay (ELISA)", comprises a test that uses antibodies and color change to identify a substance, usually an antigen, in a liquid or wet sample. Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are non-specifically bound. After the final wash step, the plate is developed by adding an enzymatic substrate to produce a visible signal, which indicates the quantity of antigen in the sample. ELISA can perform other forms of ligand binding assays instead of strictly "immuno" assays, though the name carried the original "immuno" because of the common use and history of development of this method. The technique essentially requires any ligating reagent that can be immobilized on the solid phase along with a detection reagent that will bind specifically and use an enzyme to generate a signal that can be properly quantified. In between the washes, only the ligand and its specific binding counterparts remain specifically bound or "immunosorbed" by antigen-antibody interactions to the solid phase, while the nonspecific or unbound components are washed away.

The term "multiplex assay", as used herein, comprises a type of assay that simultaneously measures multiple analytes (dozens or more) in a single run/cycle of the assay. It is distinguished from procedures that measure one analyte at a time. Multiplex assays are often used in high-throughput screening settings, where many specimens can be analyzed using a multiplex (or other) assay.

The term "manual gate", as used herein, may generally refer to the positioning of size exclusion chromatography or selective binding adsorbent materials within the microfluidic channels between the various portions of the handheld device. The term "size exclusion chromatography", as used herein, comprises a chromatographic method in which molecules in solution are separated by their size, and in some cases molecular weight. It is usually applied to large molecules or macromolecular complexes such as proteins and industrial polymers. With size exclusion chromatography, there are short and well-defined separation times and narrow bands, which lead to good sensitivity. There is also no sample loss because solutes do not interact with the stationary phase. Size exclusion chromatography works by trapping smaller molecules in the pores of the adsorbent material ("stationary phase"). The larger molecules simply pass by the pores because those molecules are too large to enter the pores. Larger molecules therefore flow through the column more quickly than smaller molecules, that is, the smaller the molecule, the longer the retention time.

The terms "microfluidic channels", "microfluidics", and "microfluidic", as used herein, refer to the manipulation of continuous liquid flow through microfabricated channels. Microfluidic channels employ passive fluid control techniques such as capillary forces. In order to consider it microfluidics, at least one dimension of the channel must be in the range of a micrometer or tens of micrometers.

The terms "ligating", "ligated", and "ligate", as used herein, refer to the joining together of linear DNA fragments with covalent bonds. More specifically, DNA ligation involves creating a phosphodiester bond between the 3' hydroxyl of one nucleotide and the 5' phosphate of another. The enzyme used to ligate DNA fragments is T4 DNA ligase, which originates from the T4 bacteriophage. This enzyme will ligate DNA fragments having blunt ends or DNA fragments having overhanging, cohesive ends that are annealed together.

The terms "degrading", "degraded", "degrade", "digesting", "digested", and "digest", as used herein, refer to the cleavage of RNA via a hydrolytic mechanism using at least one non-sequence-specific endonuclease (i.e., RNase H). RNase H's ribonuclease activity cleaves the 3'-O—P bond of RNA in a DNA/RNA duplex substrate to produce 3'-hydroxyl and 5'-phosphate terminated products. Nucleic acid identification can be achieved by the recognition and binding of target DNA by the designated RNA probe. The enzyme RNase H can selectively and repeatedly destroy only RNA probe from DNA-RNA duplexes for signal amplification to detection limit of femtomole level.

II. General Method and Device for Identifying a Target Organism

In some example embodiments, a method for identifying a target organism is provided. For instance, this method may provide, for example, a lightweight (i.e., less than 0.5 lb), cost-effective means of identifying, for instance, pathogens and/or individuals. As such, for example, the methods and devices may permit the identification of pathogens and/or individuals at sample collection sites, thereby limiting the need to ship samples to laboratories and, as a result, providing rapid readouts, thereby permitting faster identification of pathogens and/or individuals in urgent situations (e.g., disease outbreak, criminal activity, etc.). In general, methods for identifying a target organism may include extracting a nucleic acid from a sample to form an extracted nucleic acid (as seen, for example, in Ali N et al., "Current Nucleic Acid Extraction Methods and Their Implications to Point-of-Care Diagnostics," BioMed Research International, volume 2017, Article ID 9306564, (2017), 13 pages, the contents of which are incorporated herein by reference in its entirety), amplifying the extracted nucleic acid to form a nucleic acid amplicon, tagging the nucleic acid amplicon with a capture probe and a detector partner to form a detector partner-nucleic acid amplicon-capture probe complex, and performing a detection assay on the detector partner-nucleic acid amplicon-capture probe complex to identify whether the target organism is present in the sample.

In accordance with certain exemplary embodiments, for instance, amplifying the extracted nucleic acid to form the nucleic acid amplicon may comprise isothermally amplifying the extracted nucleic acid. In further embodiments, for example, isothermally amplifying the extracted nucleic acid may comprise performing nucleic acid sequence-based amplification (NASBA) on the extracted nucleic acid. Using RNA as an example, the NASBA procedure may comprise synthesizing an RNA strand from a template RNA strand utilizing a first strand synthesis primer and avian myeloblastosis virus reverse transcriptase (AMV-RT). Next, the template RNA strand may be cleaved using RNase H. A second RNA strand may then be synthesized utilizing a second strand synthesis primer and AMV-RT. Finally, the cRNA amplicon may be synthesized from the two RNA strands by using T7 RNA polymerase. By utilizing a nucleic acid amplification step, the assay sensitivity and specificity may be significantly enhanced. As seen for example in, Compton, J., "Nucleic acid sequence-based amplification," Nature, volume 350, March 1991, pages 91-92; Fahy, E., et al., "Self-sustained Sequence Replication (3SR): An Isothermal Transcriptionbased Amplification System Alternative to PCR," PCR methods Appl. 1991 volume 1(1): 25-33; Gracias, K S et al., "NUCLEIC ACID SEQUENCE-BASED AMPLIFICATION (NASBA) IN MOLECULAR BACTERIOLOGY: A PROCEDURAL GUIDE," Journal of Rapid Methods and Automation in Microbiology 15 (2007) 295-309; and Deiman, B. et al., "Characteristics and Applications of Nucleic Acid Sequence-Based Amplification (NASBA)," (2002) Molecular Biotechnology (2002) 20:163-176, the contents of which are incorporated herein by reference in their entirety.

According to certain embodiments, for instance, performing the detection assay on the detector partner-nucleic acid amplicon-capture probe complex may comprise at least one of performing a lateral flow assay or performing an enzyme-linked immunosorbent assay (ELISA). For example, see Goldmeyer J. et al., "Identification of *Staphylococcus aureus* and Determination of Methicillin Resistance Directly from Positive Blood Cultures by Isothermal Amplification and a Disposable Detection Device," J. Clin. Microbiol. 46(4): 1534-1536, 2008; Niemz, A. et. al., "Point-of-care nucleic acid testing for infectious diseases," Trends in Biotechnology, 2011, 29(55):240-250; and Rohrman, B. et al., "A Lateral Flow Assay for Quantitative Detection of Amplified HIV-1 RNA," *PLoS One*, 2012, 7(9)1-8, the contents of which are incorporated herein by reference in their entirety. In some embodiments, for example, the detection assay may comprise a multiplex assay. In further embodiments, for instance, when a multiplex assay is used, the number of target organisms that may be analyzed may comprise from about 3 targets to about 20 targets. In other embodiments, for example, the number of target organisms that may be analyzed may comprise from about 4 targets to about 15 targets. In further embodiments, for instance, the number of target organisms that may be analyzed may comprise from about 5 targets to about 10 targets. As such, in certain embodiments, the number of target organisms that may be analyzed may comprise from at least about any of the following: 2, 3, 4, and 5 targets and/or at most about 20, 19, 18, 17, 16, 15, 14, 13, 12, 11, and 10 targets (e.g., from about 4-18 targets, from about 5-19 targets, etc.).

The detection assay may be enabled to operate in a multiplex format due to the use of target-specific capture probes and detector partners for capturing amplification products. In performing the detection assay, for instance, the detector partner-nucleic acid amplicon-capture probe complex may be captured via the interaction between the capture probe and a stripped antibody positioned either on the lateral flow membrane or within an ELISA well. As a result, the capture may be visualized using the detector partner. In this regard, the detection assay may be both highly sensitive (i.e. 1 pfu/mL or 1 cfu/mL) and highly specific.

In accordance with certain exemplary embodiments, for instance, the capture probe may comprise a binding moiety (e.g., a hapten). In some embodiments, for example, the binding moiety may comprise at least one of digoxigenin (DIG), fluorescein (FITC), rhodamine, dinitrophenol (DNP), biotin (BIO), phosphorus, or any combination thereof.

In some embodiments, for example, the detector partner may comprise a biomolecule (e.g., an antibody, a protein, etc.) that selectively binds to at least one of a double stranded DNA, a DNA-RNA hybrid, a single stranded RNA, or any combination thereof. In further embodiments, for instance, the detector partner may comprise at least one of biotin, an enzyme, a gold-coated antibody, a gold-nanoparticle, a magnetic-nanoparticle, or any combination thereof. In such embodiments, for instance, the detector partner (i.e., moiety) may be bound to an anti-nucleic acid (e.g., DNA, RNA, etc.) antibody that also binds to a DNA-RNA hybrid molecule. For example, gold-nanoparticles may be used for measuring heat generation after infrared exposure of bands of captured tagged amplicons-nanoparticles complex. Gold-nanoparticles exposed to infrared laser sources may generate intense localized heat (see, for example, Mathiyazhakan M. et al., "A Concise Review of Gold Nanoparticles-Based Photo-Responsive Liposomes for Controlled Drug Delivery," Nano-Micro Letters (2018) 10:10). In one embodiment, the anti-DNA/RNA antibody will be coated with gold-nanoparticles and incubated with an RNA amplicon product that has been hybridized to a biotin carrying DNA probe. The complex of DNA/RNA and gold-nanoparticle Ab will be loaded onto a well coated with streptavidin which will bind to the complex via the interaction of biotin-streptavidin. If the NASBA did not generate RNA amplicon, the gold-nanoparticle Ab will be washed away during the subsequent wash steps. If RNA is generated, only if the target template is present, then DNA/RNA will form followed with the larger gold-nanoparticle complex. The resulting complex captured/enriched in the streptavidin well can be detected following infrared radiation by measuring the resultant heat generation, which can be used to analyze the presence of RNA generation from the amplication reaction. The resulting change in temperature at the respective spot on the membrane may be correlated to assign the presence of the corresponding biological agent that the tags have been specifically designed to recognize. Moreover, heat intensities at each spot may be used to quantify the respective biological agents present in the sample. In other embodiments, for instance, magnetic-nanoparticles may be used for measuring the magnetic field of bands generated by captured tagged amplicons-nanoparticles complex. The amount of magnetized particles captured at each respective spot on the membrane may be correlated to assign the presence of the corresponding biological agent that the tags are specifically designed to recognize. Moreover, magnetic field measurements at each spot may be used to quantify the respective biological agents present in the sample.

In accordance with certain exemplary embodiments, for instance, the method may further comprise performing size exclusion chromatography or other selective binding between extracting the nucleic acid and amplifying the extracted nucleic acid, and amplifying the extracted nucleic acid and tagging the nucleic acid amplicon. In this regard, the size exclusion chromatography may act as manual gates between each of the steps to only allow the molecules of interest through to the next step.

In some embodiments, for example, the method may further comprise adding a flow buffer to the detector partner-nucleic acid amplicon-capture probe complex prior to performing the detection assay on the detector partner-nucleic acid amplicon-capture probe complex. For instance, the flow buffer may comprise any suitable buffer (e.g., phosphate-buffered saline (PBS)) for use in conjunction with the methods and devices discussed herein as understood by one of ordinary skill in the art.

Figure 2:
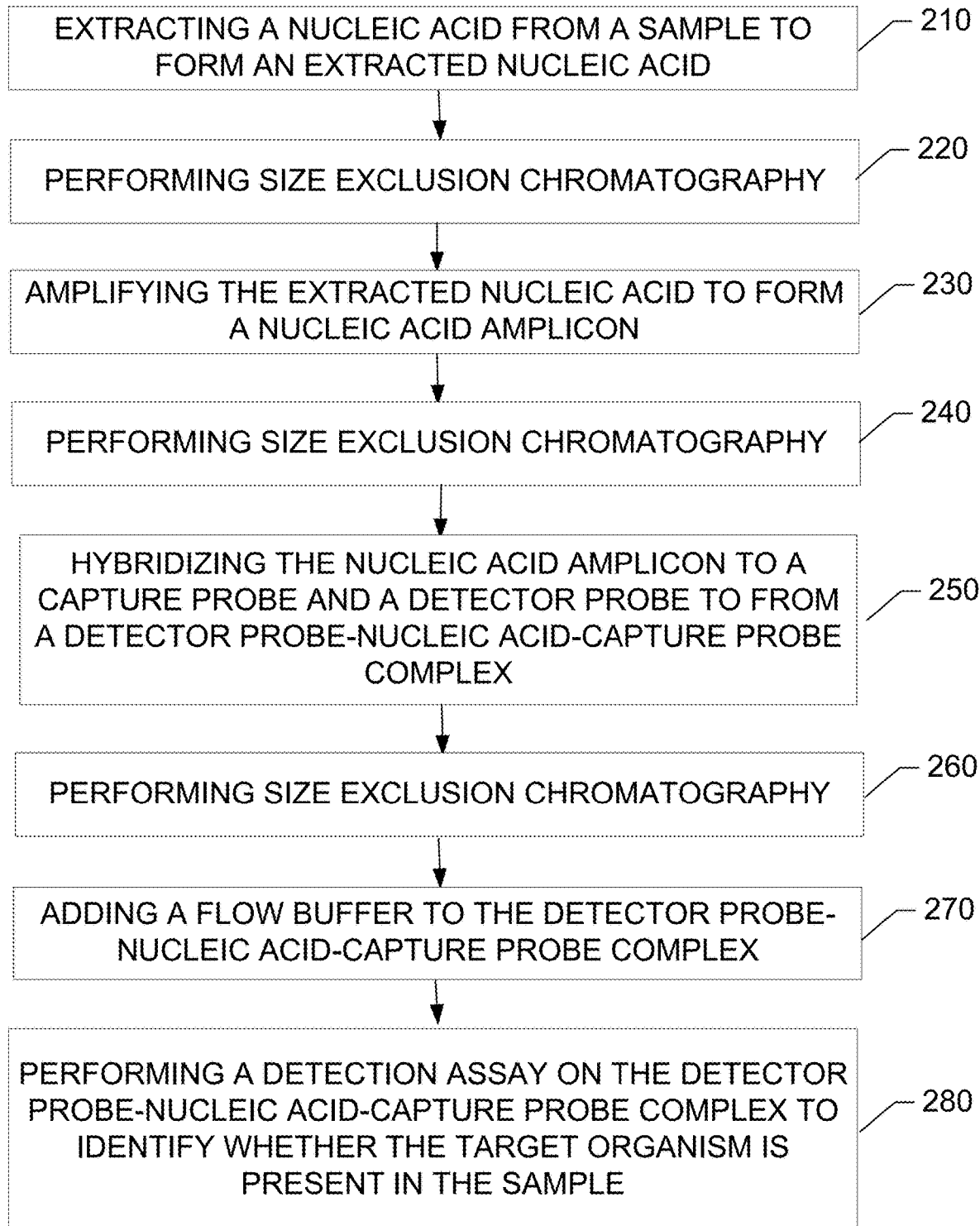
FIG. 2 illustrates a block diagram of a method for identifying a target organism including the optional steps of performing size exclusion chromatography according to an example embodiment.

FIG. 1, for example illustrates an overview of a method for identifying a target organism according to an example embodiment. As shown in FIG. 1, the overview 10 includes various sample collection sites (e.g., hospitals, insects, laboratories, crime scenes, the environment, etc.), sample types (e.g., cultures, blood, mucus, soil, etc.), nucleic acid target extraction, and rapid pathogen or human identification using the device described herein. FIG. 2, for instance, illustrates a block diagram of a method for identifying a target organism including the optional steps of performing size exclusion chromatography according to an example embodiment. As shown in FIG. 2, the method includes extracting a nucleic acid (see, for example Ali N et al., "Current Nucleic Acid Extraction Methods and Their Implications to Point-of-Care Diagnostics," BioMed Research International, volume 2017, Article ID 9306564, (2017), 13 pages) from a sample to form an extracted nucleic acid at operation 210, the optional step of performing size exclusion chromatography at operation 220, amplifying the extracted nucleic acid to form a nucleic acid amplicon at operation 230, the optional step of performing size exclusion chromatography at operation 240, hybridizing the nucleic acid amplicon to a capture probe labeled with a unique moiety (e.g., biotin) to form DNA/RNA hybrid and followed with binding to a detector partner (e.g., an antibody that recognizes and selectively binds to DNA/RNA hybrids that is labeled with a reporter moiety (e.g., fluorophore)) to form a detector partner-nucleic acid amplicon-capture probe complex at operation 250, adding a flow buffer to the detector partner-nucleic acid amplicon-capture probe complex at operation 260, the optional step of performing a membrane chromatography step at operation 270, and performing a detection assay on the detector partner-nucleic acid amplicon-capture probe complex to identify whether the target organism is present in the sample at operation 280.

III. Method and Device for Identifying a Target Biological Agent

In accordance with certain exemplary embodiments, for instance, the target organism may comprise a biological agent. In general, methods for identifying a target biological agent may include extracting a nucleic acid from a sample to form an extracted nucleic acid, amplifying the extracted nucleic acid to form a nucleic acid amplicon, tagging the nucleic acid amplicon with a capture probe, forming a detector partner amplicon-capture probe complex, immobilizing the complex via an interaction between a moiety on the capture probe and a pre-coated binding partner (e.g., biotin and streptavidin), removing unbound component by an optional washing step with the flow buffer and detecting the bound complex by assessing the signal from the detector partner (e.g., visualization of bound gold-nanoparticles) to identify whether the target organism is present in the sample. The detector partner can specifically be present at the capture zone if only the amplicon is present and the amplification reaction can only generate the amplicon if the target organism is present in the biological sample that was added into the amplication reaction.

Figure 3:
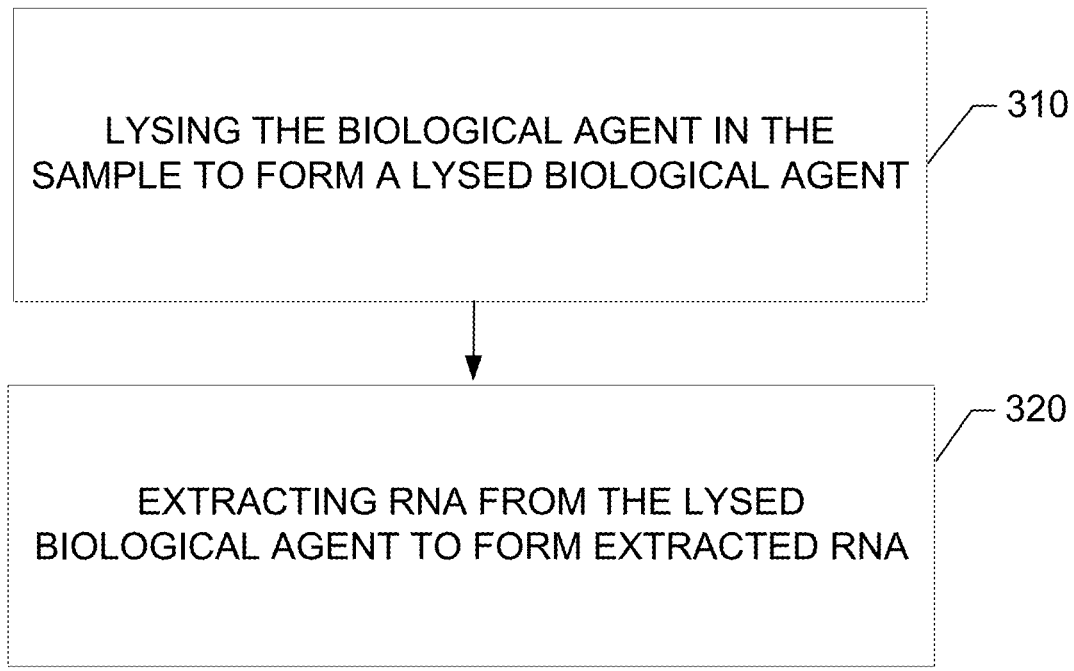
FIG. 3 illustrates a block diagram of extracting a nucleic acid from a sample to form an extracted nucleic acid when the target organism is a biological agent according to an example embodiment.

In such embodiments, for example, extracting the nucleic acid from the sample to form the extracted nucleic acid may comprise lysing the biological agent in the sample to form a lysed biological agent, and extracting RNA from the lysed biological agent to form extracted RNA. For instance, RNA may be extracted by any suitable extraction method that is compatible with the methods and devices discussed herein as understood by one of ordinary skill in the art. Current commercially available nucleic acid extraction protocols have been described by, for example, Ali N et al., "Current Nucleic Acid Extraction Methods and Their Implications to Point-of-Care Diagnostics," BioMed Research International, volume 2017, Article ID 9306564, (2017), 13 pages. In this regard, the sample extraction and preparation may be integrated into the methods and devices disclosed herein. FIG. 3, for instance, illustrates a block diagram of extracting a nucleic acid from a sample to form an extracted nucleic acid when the target organism (where the amplification probes are designed for specific target organisms that have been previously identified (see below)) is a biological agent according to an example embodiment. As shown in FIG. 3, extracting a nucleic acid from a sample to form an extracted nucleic acid when the target organism is a biological agent includes lysing the biological agent in the sample to form a lysed biological agent at operation 310 and extracting RNA from the lysed biological agent to form extracted RNA at operation 320.

Figure 4:
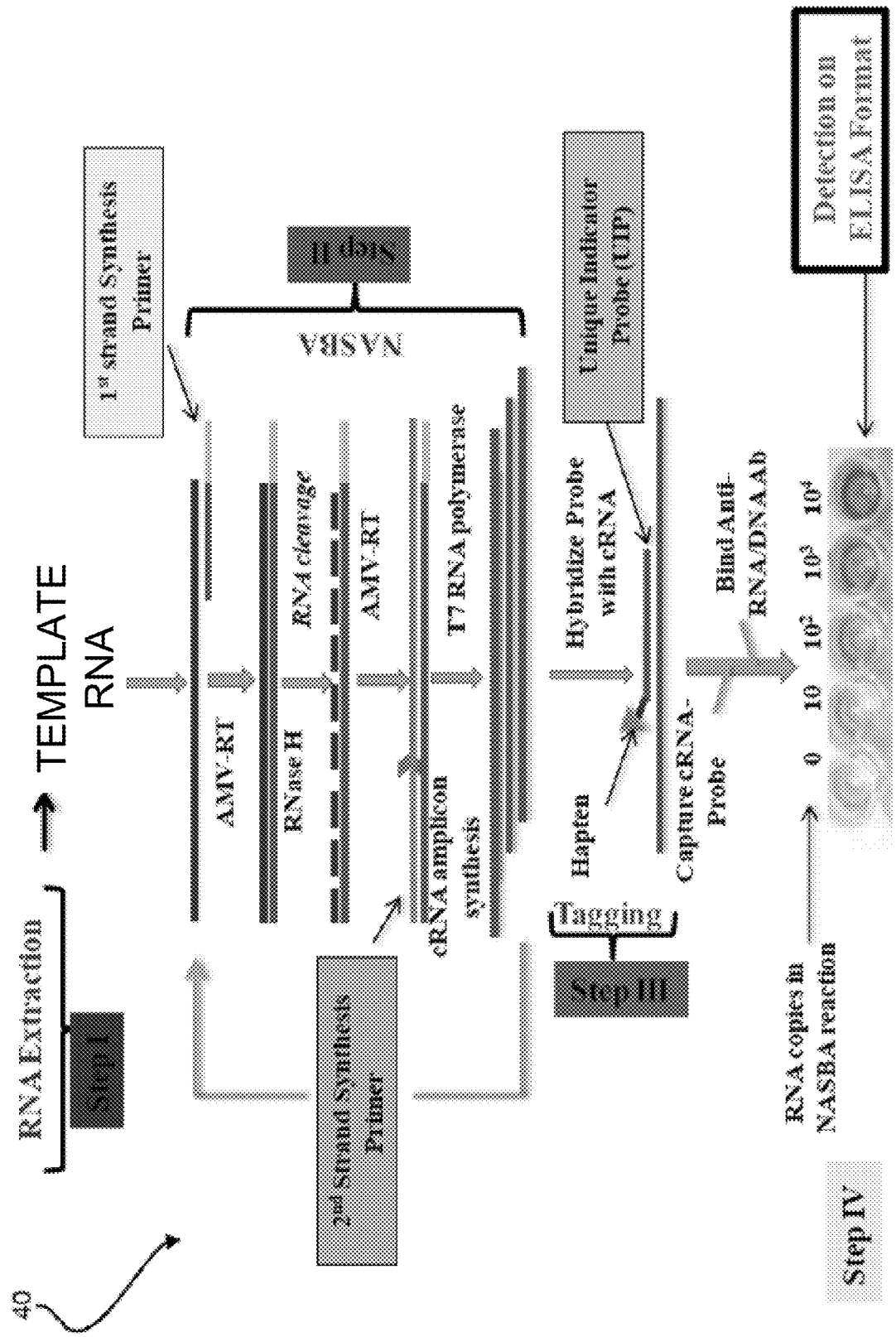
FIG. 4 illustrates an overview of a method for identifying a target biological agent according to an example embodiment.
Figure 5:
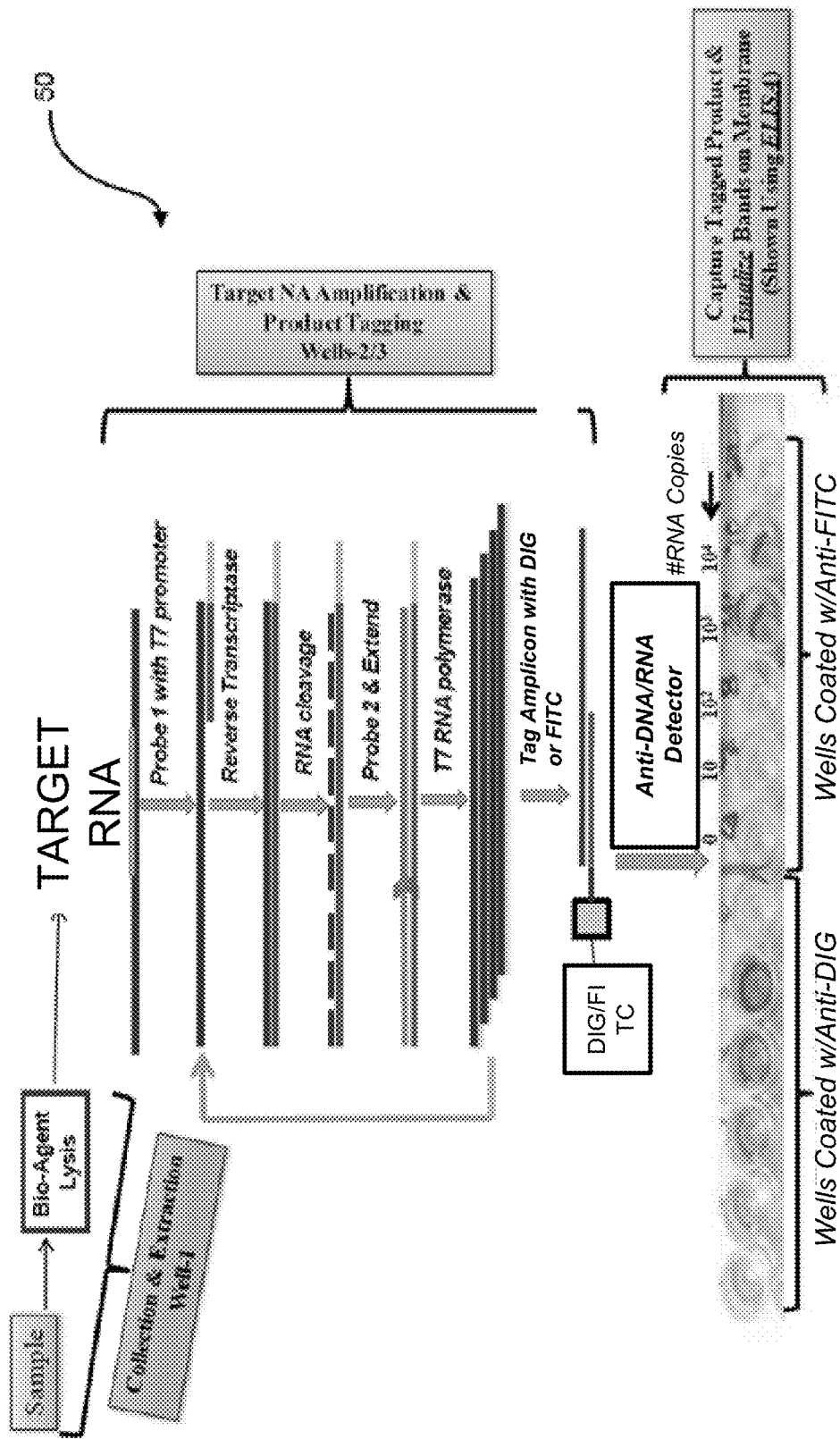
FIG. 5 illustrates an overview of a method for identifying a target biological agent according to an example embodiment.

FIGS. 4 and 5, for example, illustrate an overview of a method for identifying a target biological agent according to an example embodiment. As shown in FIGS. 4 and 5, the overviews 40 and 50 include RNA extraction, NASBA designed to amplify target organisms by including specific primer sets that only amplify extracted RNA segments from an organism based on the RNA sequence (organism sequences can be obtained from open source databases such as PubMed), tagging of the RNA amplicon, and detection using ELISA.

In another aspect, certain exemplary embodiments provide a handheld device for identifying a target organism (e.g., a target biological agent), based on the design of the NASBA primer sets. The NASBA reaction primers can be designed and formulated for each RNA sequence of target organism of interest. According to certain embodiments, for example, the device may include a nucleic acid extraction portion, the nucleic acid extraction portion being configured to extract nucleic acid from a sample to form extracted nucleic acid; a nucleic acid amplification portion, the nucleic acid amplification portion being configured to amplify the extracted nucleic acid to form a nucleic acid amplicon; a tagging moiety attached to a capture probe (e.g., biotin), the hybridization of the capture probe to the amplicon, and the binding of the hybridized amplicon to a detector partner to form a detector partner-amplicon-capture probe complex; and to immobilize the complex to a surface pre-coated with a partner via the selective interaction of the coated partner with the tagging moiety attached to the capture probe followed with assessing the bound detector partner-amplicon-capture probe complex.

Figure 15B:
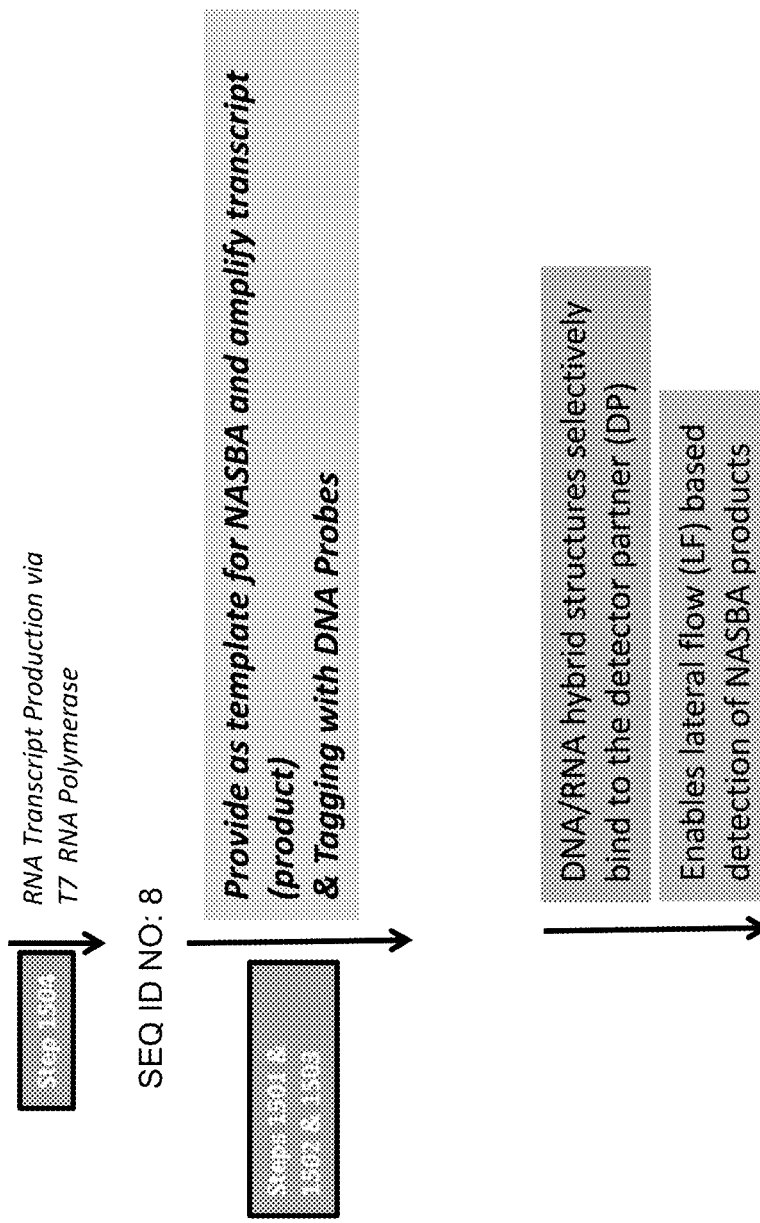

FIGS. 15A and 15B is an example flowchart illustrating the Nucleic Acid Sequence-Based Amplification reaction that targets, for example, a segment of the Ebola virus L gene (AF086833) sequence. In FIG. 15A, step 1501, NASBA Probe T7 Probe Hybridization Step-One RT catalyzed synthesis, entails hybridization of the forward primer (carrying T7 promoter sequence) to the 3'-end of the virus RNA. In step 1502, first strand Synthesis and reverse Probe hybridization, is the extension of the said forward primer via reverse transcriptase (RT) catalyzed reaction to generate the first strand, complementary DNA strand, followed by the hybridization of the reverse primer at the 5'-end of the said first strand. In step 1503, the second strand synthesis occurs; the extension of the reverse primer via reverse transcriptase (RT) catalyzed reaction to generate the second DNA strand that is the complementary DNA strand. The method continues to FIG. 15B with step 1504, with RNA Transcript Production via T7 RNA Polymerase, and entails the exponential generation of cRNA (complementary sequence to the initial target viral RNA) via T7 RNA polymerase de novo RNA synthesis starting at the 3'-end of the T7 promoter sequence introduced at the 5'-end of the forward primer. Followed the amplification steps, the cRNA is then tagged with the respective tagging probes (TP) to form DNA/RNA hybrids. These DNA/RNA hybrid structures selectively interact with the detector partner (DP) which provide the basis for an immunoassay based detection—suitable for portable detection.

In accordance with certain exemplary embodiments, for instance, the device may further comprise a flow buffer application portion, the flow buffer application portion being configured to add a flow buffer to the detector partner-nucleic acid amplicon-capture probe complex; at least three manual gates, one of the at least three manual gates being positioned between each of the nucleic acid extraction portion and the nucleic acid amplification portion, the nucleic acid amplification portion and the tagging portion, and the tagging portion and the detection portion; and a plurality of microfluidic channels positioned between each of the nucleic acid extraction portion and the nucleic acid amplification portion, the nucleic acid amplification portion and the tagging portion, and the tagging portion and the detection portion. Moreover, according to some embodiments, for example, the device may comprise micro-batteries (e.g., lithium coin cell batteries) to enable the nucleic acid extraction portion, the nucleic acid amplification portion, and the tagging portion in order to maintain adequate extraction, amplification, and tagging temperatures and flow conditions within these portions.

According to certain embodiments, for instance, the device may comprise a sample loading base microfluidics connection between the sample loading based, amplification well, capture tagging well, complex formation with detector partner well and a membrane strip that contains a binding zone to immobilize the capture probe and to enable the visualization of the bound detector partner. This embodiment is a modification of a current lateral flow based detection platform such as is described in, for example, Fang, Xueen, et al., "Predicting viruses accurately by a multiplex microfluidic loop-mediated isothermal amplification chip," Analytical Chemistry (2011) 83:690-695; and Sun, Jiashu, et al., "Point-of-care biochemical assays using gold nanoparticle-implemented microfluidics," Chem. Soc. Rev., 2014, 43, 6239-6253, the contents of which are incorporated herein by reference in their entirety. In some embodiments, for example, the base may comprise at least one micro-battery, infrared laser sources, temperature and/or magnetic field scanners and/or the like. In further embodiments, for instance, the strip may be disposable, while the base may be reusable for analyzing multiple samples.

Figure 6:
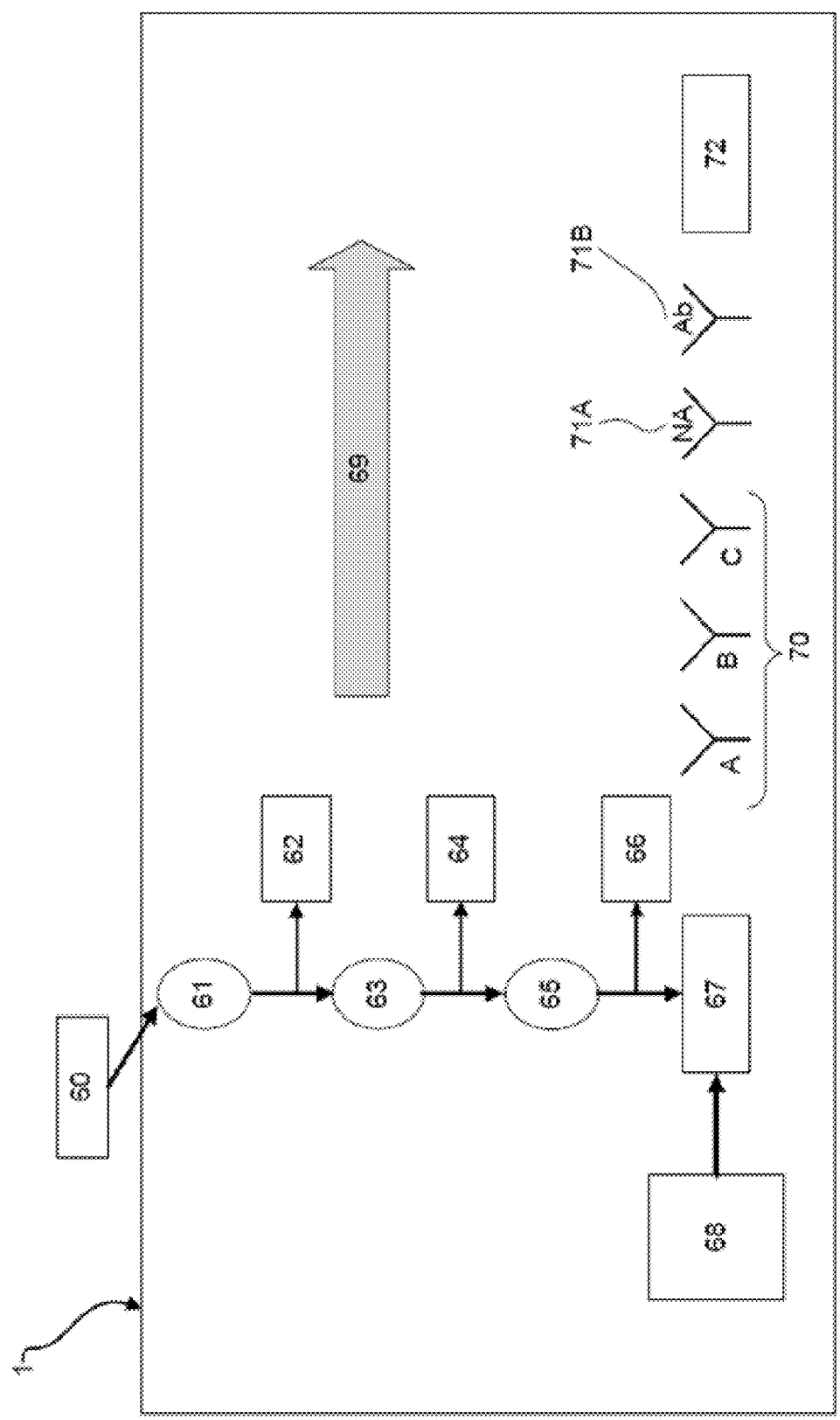
FIG. 6 illustrates a schematic for a handheld device for identifying a target biological agent according to an example embodiment.

FIG. 6, for instance, illustrates a schematic for a handheld device for identifying a target biological agent according to an example embodiment. As shown in FIG. 6, the device 1 includes an extraction well 61, an amplification well 63, and a tagging well 65 prior to the detection assay portion. Each of the extraction well 61, amplification well 63, tagging well 65, and conjugate pad 67 of the detection assay are separated by manual gates 62, 64, and 66 respectively, which utilize size exclusion chromatography or other selective binding to determine what molecules continue to the next well. To operate the device 1, an environmental or clinical sample to be interrogated for the presence of an organism of interest 60 is placed in the extraction well 61. After processing in the extraction well 61 (as shown in, for example, Ali N et al., "Current Nucleic Acid Extraction Methods and Their Implications to Point-of-Care Diagnostics," BioMed Research International, volume 2017, Article ID 9306564, (2017), 13 pages, the contents of which are incorporated herein by reference in its entirety), the extracted nucleic acid flows through manual gate 62 and to amplification well 63. After amplification, the nucleic acid amplicon flows through manual gate 64 and to tagging well 65. After hybridizing with the capture probe and the detector partner, the detector partner-nucleic acid amplicon-capture probe complex flows through manual gate 66 and to conjugate pad 67. Flow buffer is provided from flow buffer portion 68 to push the complex through the detection assay in the flow direction 69, where the complex encounters bound antibodies 70, a nucleic acid control 71A, and an antibody control 71B before ending at the absorbent pad 72.

Figure 16:
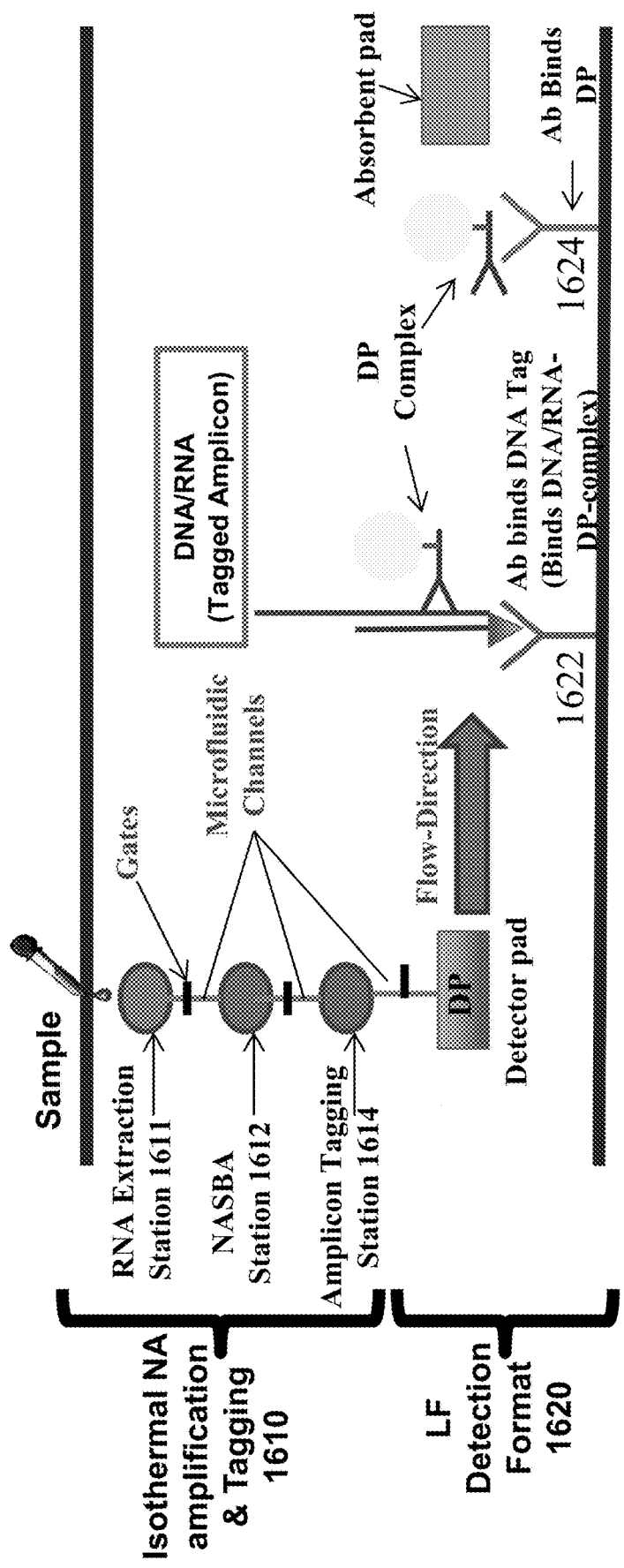
FIG. 16 illustrates another example design for a handheld device for identifying a target biological agent according to an example embodiment.

FIG. 16, for instance, illustrates another example schematic for a handheld device for identifying a target biological agent according to an example embodiment. FIG. 16 demonstrates the feasibility of the described approach for the development detection/diagnostic solution that includes, the use of an exquisitely sensitive molecular amplification assay coupled with an immunoassay detection which is suitable for portable device development. Segment 1610 describes sections related to the isothermal amplification steps involved to generate an exponential amount of detectable complementary RNA. Whereas segment 1620 describes a lateral flow section to for the binding of the DNA/RNA hybrids (tagged cRNA) to the DP to enable detection by visualization of bands. Station 1611 includes RNA extraction (unless RNA extraction is performed manually). Station 1612 includes NASBA. At station 1614, the tagging of the cRNA tagging probe/s (TP) is performed to form the DNA/RNA hybrid. The detector partner (DP) adsorbed on a pad will then complex with DNA/RNA structures upon reconstitution with reaction mix. If DNA/RNA complex present, depending on the presence of the targeted NA in 1612 (the NASBA station), the DNA/RNA-DP complex will be detected at position 1622 (entails positive result). At position 1624, the DP will be visualized as a positive control for the LF process, and if the NASBA did not generate an RNA amplicon signal will be visualized at position 1624 (entails negative result).

According to certain embodiments, for example, the target biological agent may comprise at least one of a virus, a bacterium, or any other suitable protein-based biological agent (e.g., pathogen) as understood by one of ordinary skill in the art. For example, RNA sequences that are amenable for amplification reaction have been provided for Ebola virus, Marburg virus, Rift valley fever virus, dengue virus and yellow fever virus by, for example, Drosten, C. et al., "Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription-PCR," J. Clin.

Microbiol., 2002, 40 (7); 2323-2330; and Wu et al., "Detection of Dengue Viral RNA Using a Nucleic Acid Sequence-Based Amplification Assay," J. Clin. Microbiol., 2001, 39 (8); 2794-2798, the contents of which are hereby incorporated by reference in their entirety. In a specific format, the NASBA amplification mix can be formulated with primer sets that target the L gene sequence of Ebola virus (GenBank number #AF086833), and the GPC gene sequence of Lassa Virus (GenBank #J04324.1) and the 3' noncoding region of dengue virus (GenBank #M87512.1) and the L gene sequence of yellow fever virus ((GenBank #002031.1), the contents of which are incorporated herein by reference in their entirety. The cited viruses such as Ebola, yellow fever, dengue, etc., are provided as examples to show proof-of-concept on the method provided, the approach is universal to all viruses. One embodiment describes a method of detection rather than the detection of a specific virus. If Ebola mutates, the target becomes the new mutated virus using the same method. The described method provides the ability, for example, to shrink current devices and makes them more portable to ensure feasibility to detect pathogens at site of sample collection, for example. However, the rate of virus mutation is another problem and is an issue for all current methods.

| Pathogen Name | Sample Sequence |
| --- | --- |
| Ebola Virus L gene | 5'SEQ ID NO: 1 3' |
| Lassa Virus GPC | 5'SEQ ID NO: 2 3' |
| Dengue Virus type 1 3' noncoding region | 5'SEQ ID NO: 3 3' |
| Yellow Fever Virus L gene | 5'SEQ ID NO: 4 3' |

For example, the target biological agent may comprise a virus including, but not limited to, a flavivirus, an alphavirus, a bromovirus, an arterivirus, an aphthovirus, a rhinovirus, a hepatovirus, a cardiovirus, a cosavirus, a dicipivirus, an erbovirus, a kobuvirus, a megrivirus, a parechovirus, a piscevirus, a salivirus, a sapelovirus, a senecavirus, a teschovirus, a tremovirus, a potyvirus, a coronavirus, a norovirus, an orthomyxovirus, a rotavirus, a picobirnavirus, an enterovirus, a bymovirus, a comovirus, a nepovirus, a nodavirus, a picornavirus, a sobemovirus, a luteovirus, a carmovirus, a dianthovirus, a pestivirus, a tombusvirus, a bacteriophage, a carlavirus, a furovirus, a hordeivirus, a potexvirus, a rubivirus, a tobravirus, a tricornavirus, a tymovirus, and/or the like. In further embodiments, for example, the target biological agent may comprise a virus including, but not limited to, dengue virus (e.g., DENV1, DENV2, DENV3, DENV4), West Nile virus, absettarov virus, alkhurma virus, deer tick virus, gadgets gully virus, kadam virus, karshi virus, kyasanur forest disease virus, Langat virus, louping ill virus, omsk hemorrhagic fever virus, powassan virus, royal farm virus, sokuluk virus, tick-borne encephalitis virus, Turkish sheep encephalitis virus, kama virus, meaban virus, Saumarez Reef virus, tyuleniy virus, *Aedes* flavivirus, barkedji virus, calbertado virus, cell fusing agent virus, chaoyang virus, *Culex* flavivirus, *Culex theileri* flavivirus, donggang virus, ilomantsi virus, Kamiti River virus, lammi virus, marisma mosquito virus, nakiwogo virus, nhumirim virus, nounane virus, Spanish *Culex* flavivirus, Spanish ochlerotatus flavivirus, quang binh virus, aroa virus, bussuquara virus, kedougou virus, cacipacore virus, koutango virus, ilheus virus, Japanese encephalitis virus, Murray Valley encephalitis virus, alfuy virus, rocio virus, St. Louis encephalitis virus, usutu virus, yaounde virus, kokobera virus, bagaza virus, baiyangdian virus, duck egg drop syndrome virus, Jiangsu virus, Israel turkey meningoencephalomyelitis virus, ntaya virus, tembusu virus, zika virus, banzi virus, bouboui virus, edge hill virus, jugra virus, saboya virus, sepik virus, Uganda S virus, wesselsbron virus, yellow fever virus, Entebbe bat virus, yokose virus, apoi virus, vowbone ridge virus, Jutiapa virus, modoc virus, sal vieja virus, san perlita virus, bukalasa bat virus, Carey Island virus, Dakar bat virus, *Montana myotis* leukoencephalitis virus, Phnom Penh bat virus, Rio Bravo virus, soybean cyst nematode virus 5, *Aedes cinereus* flavivirus, *Aedes vexans* flavivirus, Coxsackievirus, echovirus, Enterovirus A, Enterovirus B, Enterovirus C, Enterovirus D, Enterovirus E, Enterovirus F, Enterovirus G, Enterovirus H, Enterovirus J, Rhinovirus A, Rhinovirus B, Rhinovirus C, poliovirus, bovine viral diarrhea virus, sindbis virus, hepatitis C, Barmah Forest virus, eastern equine encephalitis virus, Middelburg virus, ndumu virus, bebaru virus, chikungunya virus, mayaro virus, una virus, o'nyong nyong virus, Igbo-Ora virus, Ross River virus, getah virus, sagiyama virus, Semliki Forest virus, me tri virus, cabassou virus, Everglades virus, mosso das pedras virus, mucambo virus, paramana virus, pixuna virus, Rio Negro virus, trocara virus, Bijou Bridge virus, Venezuelan equine encephalitis virus, aura virus, babanki virus, kyzylagach virus, ockelbo virus, whataroa virus, Buggy Creek virus, Fort Morgan virus, Highlands J virus, western equine encephalitis virus, salmon pancreatic disease virus, sleeping disease virus, southern elephant seal virus, tonate virus, Brome mosaic virus, equine arteritis virus, foot-and-mouth disease virus, bovine rhinitis A virus, bovine rhinitis B virus, equine rhinitis A virus, aquamavirus A, duck hepatitis A virus, encephalomyocarditis virus, theilovirus, cosavirus A, cadicivirus A, equine rhinitis B virus, hepatitis A virus, aichivirus A, aichivirus B, aichivirus C, melegrivirus A, human parechovirus, Ljungan virus, fathead minnow picornavirus, salivirus A, porcine sapelovirus, simian sapelovirus, avian sapelovirus, Seneca Valley virus, porcine teschovirus, avian encephalomyelitis virus, potato virus A, SARS, Human coronavirus 229E, Human coronavirus OC43, New Haven coronavirus, Human coronavirus HKU1, Middle East respiratory syndrome coronavirus, infectious bronchitis virus, porcine coronavirus, bovine coronavirus, feline coronavirus, canine coronavirus, turkey coronavirus, ferret enteric coronavirus, ferret systemic coronavirus, pantropic canine coronavirus, porcine epidemic diarrhea virus, Ebola virus, measles virus, Influenza virus A, Influenza virus B, Influenza virus C, isavirus, thogotovirus, quaranjavirus, Norwalk virus, Hawaii virus, Snow Mountain virus, Mexico virus, Desert Shield virus, Southampton virus, Lordsdale virus, Wilkinson virus, bluetongue virus, hepatitis E virus, apple chlorotic leaf spot virus, beet yellows virus, Rubella virus, Marburg virus, Mumps virus, Nipah virus, Hendra virus, RSV, NDV, Rabies virus, Nyavirus, Lassa virus, Hantavirus, Crimean-Congo hemorrhagic fever, hepatitis D virus, Nyamanini virus, Midway virus, and/or the like.

In other embodiments, for instance, the target biological agent may comprise a bacterium including, but not limited to, *Salmonella typhi, Rickettsia prowazekii, Rickettsia typhi, Orientia tsutsugamushi, Rickettsia australis, Streptococcus pneumonia, Haemophilus influenza, Streptococcus pyogenes, Neisseria meningitides, Bacillus anthracis, Clostridium tetani, Mycobacterium tuberculosis, Mycobacterium bovis, Bordetella pertussis, Vibrio cholera, Corynebacterium diphtheria, Clostridium botulinum, Yersinia pestis*, and/or the like.

IV. Method and Device for Identifying a Human Individual

In accordance with certain exemplary embodiments, for instance, the target organism may comprise a human individual. The main objective of the invention provides a novel portable approach to determine specific nucleotide compositions at specific position in human genome to delineate single nucleotide polymorphisms (SNPs). The SNP signatures are then used to profile an individual and potential contribute to establish attribution based on a DNA samples collected. In one embodiment, a list of known markers (e.g., mitochondrial DNA hypervariable regions) that are associated with specific humans is stored in, for example, a searchable database (e.g., The Database of Short Genetic Variation (dbSNP), Kitts A, Phan L, Ward M H, and Holmes J B. In The NCBI Handbook [Internet], 2nd ed. (2014); and the dbSNP: Database for Short Genetic Variations Catalog of nucleotide changes for human and other model organisms located on the ncbi.nlm.nih.gov/snp/website) and results will be compared with a database that have the known markers. Methods for identifying a target human individual may include extracting a nucleic acid from a sample to form an extracted nucleic acid, amplifying the extracted nucleic acid to form a nucleic acid amplicon, tagging the nucleic acid amplicon with a capture probe and a detector partner to form a detector partner-nucleic acid amplicon-capture probe complex, and performing a detection assay on the detector partner-nucleic acid amplicon-capture probe complex to identify whether the target SNP signature is present in the sample.

In such embodiments, for example, extracting the nucleic acid from the sample to form the extracted nucleic acid may comprise extracting mitochondrial DNA (mtDNA) from the sample to form extracted mtDNA. For instance, extracting the mtDNA may comprise any suitable mtDNA extraction method compatible with the methods and devices discussed herein as understood by one of ordinary skill in the art.

In some embodiments, for instance, the nucleic acid amplicon may comprise an RNA amplicon and an mtDNA amplicon, and the method may further comprise cleaving the extracted mtDNA to form cleaved mtDNA segments, hybridizing the RNA amplicon to amplification primers, and concurrently performing DNA strand displacement on the cleaved mtDNA segments and amplifying the cleaved mtDNA segments to form the mtDNA segment amplicon. In such embodiments, for example, the mtDNA segment amplicon may comprise a single nucleotide polymorphism (SNP). The amplification primers may comprise forward and reverse primers with the reverse primers comprising a T7 RNA polymerase promoter sequence. In this regard, RNA transcripts may be generated by combining strand displacement using Φ-29 DNA polymerase with T7-RNA-polymerase.

In further embodiments, for instance, tagging the mtDNA segment amplicon with the capture probe and the detector partner to form the detector partner-nucleic acid amplicon-capture probe complex may comprise hybridizing the capture probe to the SNP at a 5'-terminus, and hybridizing the detector partner to the SNP at a 3'-terminus to form the detector partner-nucleic acid amplicon-capture probe complex. The capture probe may instead be hybridized to the SNP at the 3'-terminus, and the detector partner may be hybridized to the SNP at the 5'-terminus. In some embodiments, for example, the detector partner may be labeled at its 5'-end with a detector moiety. Moreover, in further embodiments, for instance, the capture probe may be labeled at its 3'-end with a capture moiety and its 5'-end with phosphate. The capture probe and the detector partner may be covalently linked to the SNP. In this regard, multiple capture and detector partner pairs may be efficiently hybridized immediately adjacent to each desired SNP.

In some embodiments, for example, the method may further comprise ligating the detector partner-nucleic acid amplicon-capture probe complex, and degrading the RNA amplicon after tagging the mtDNA amplicon with the capture probe and the detector partner. In certain embodiments, for instance, ligating the detector partner-nucleic acid amplicon-capture probe complex may comprise T4 DNA ligation. In some embodiments, for instance, degrading the RNA amplicon may comprise degrading the RNA amplicon with RNase (e.g., RNase H). During the degradation step, for example, un-ligated probes may dissociate. As such, for instance, only ligated probes may be visualized during the detection assay. Following detection via the detection assay, streptavidin conjugates may be used as a secondary labeling method to detect biotinylated molecules in order to confirm the identified SNP composition. As such, if ligation occurred, then the SNP composition may be confirmed, but if ligation did not occur, the streptavidin conjugates will not provide SNP detection. In this regard, ligation of complementary probe pairs hybridized to the RNA at each SNP may occur, while probe pairs that are mismatched remain un-ligated. Moreover, ligated probes may be captured via the detection assay (e.g., the membrane of a lateral flow device) via an interaction between the unique moiety on each capture probe and an antibody embedded in the assay. As such, the base composition at each SNP site may be delineated to generate unique individualized mtDNA signatures for DNA biometrics applications. In addition, targeting mtDNA may enable extraction of DNA biometrics information from degraded DNA samples, which is highly desirable for field-forward applications.

Figure 7:
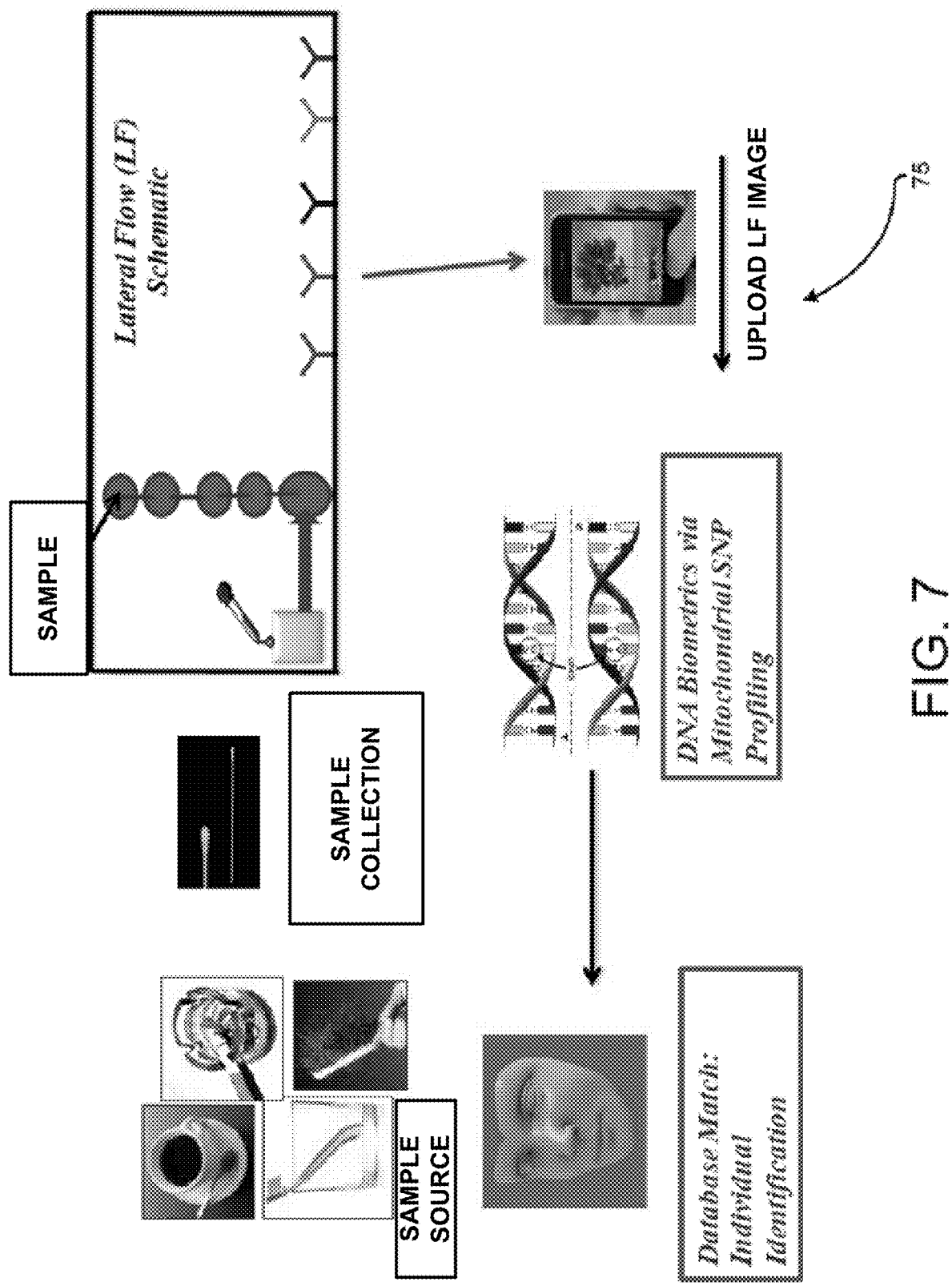
FIG. 7 illustrates an overview of a method for identifying a target human individual according to an example embodiment.

FIG. 7, for example, illustrates an overview of a method for identifying a target human individual according to an example embodiment. As shown in FIG. 7, the overview 75 includes the collection of samples from a sample source (e.g., hairbrush, toothbrush, cups, ashtrays, etc.), processing of the sample through a device as discussed herein, the upload of the lateral flow results image, DNA biometric analysis using mitochondrial SNP profiling, and individual identification using a database.

Figure 8:
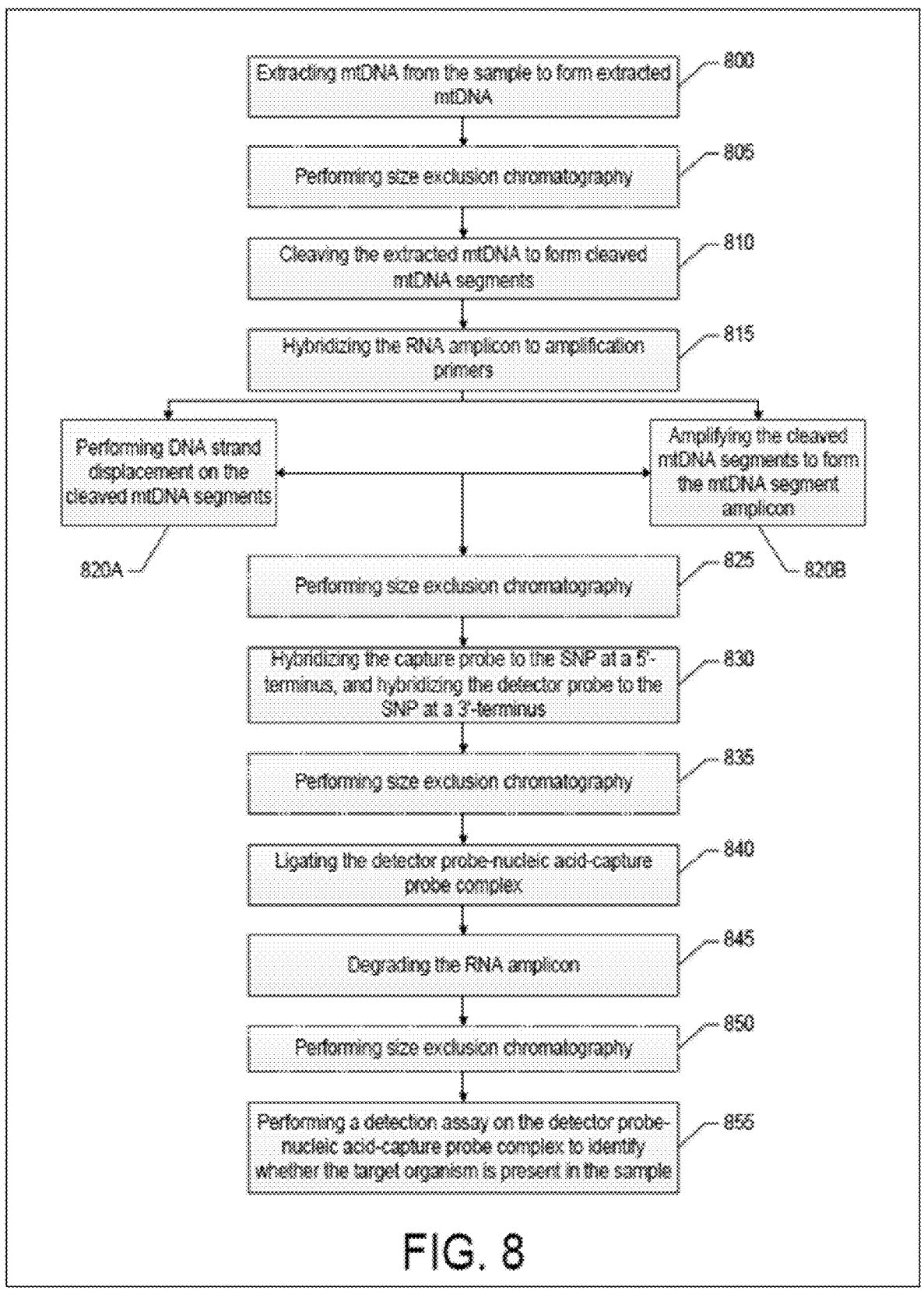
FIG. 8 illustrates a block diagram of a method for identifying a target human individual including the optional steps of performing size exclusion chromatography according to an example embodiment.
Figure 9:
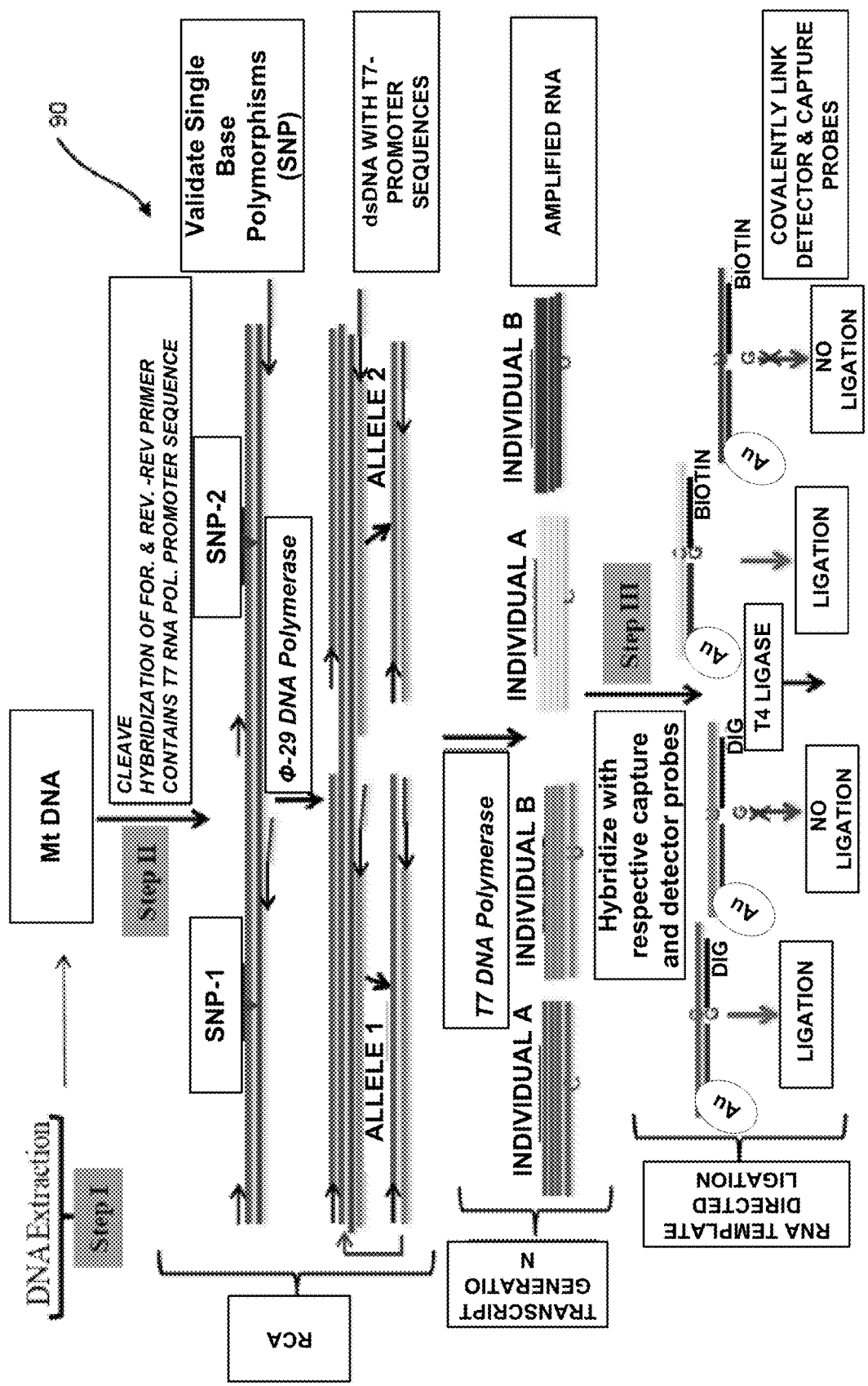
FIG. 9 illustrates a detailed overview of a method for identifying a target human individual according to an example embodiment.
Figure 10:
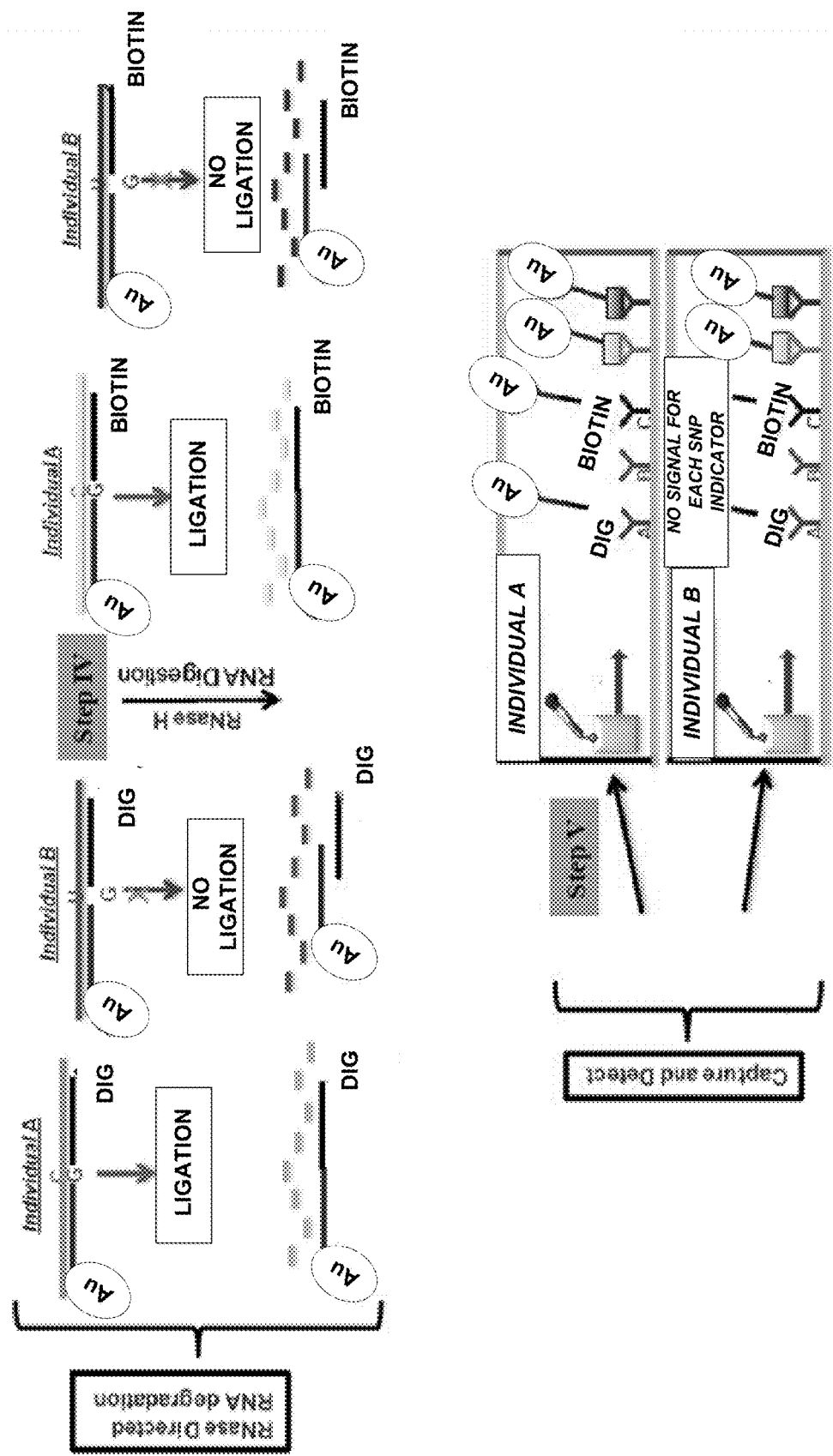
FIG. 10 illustrates a detailed overview of a method for identifying a target human individual according to an example embodiment.
Figure 11:
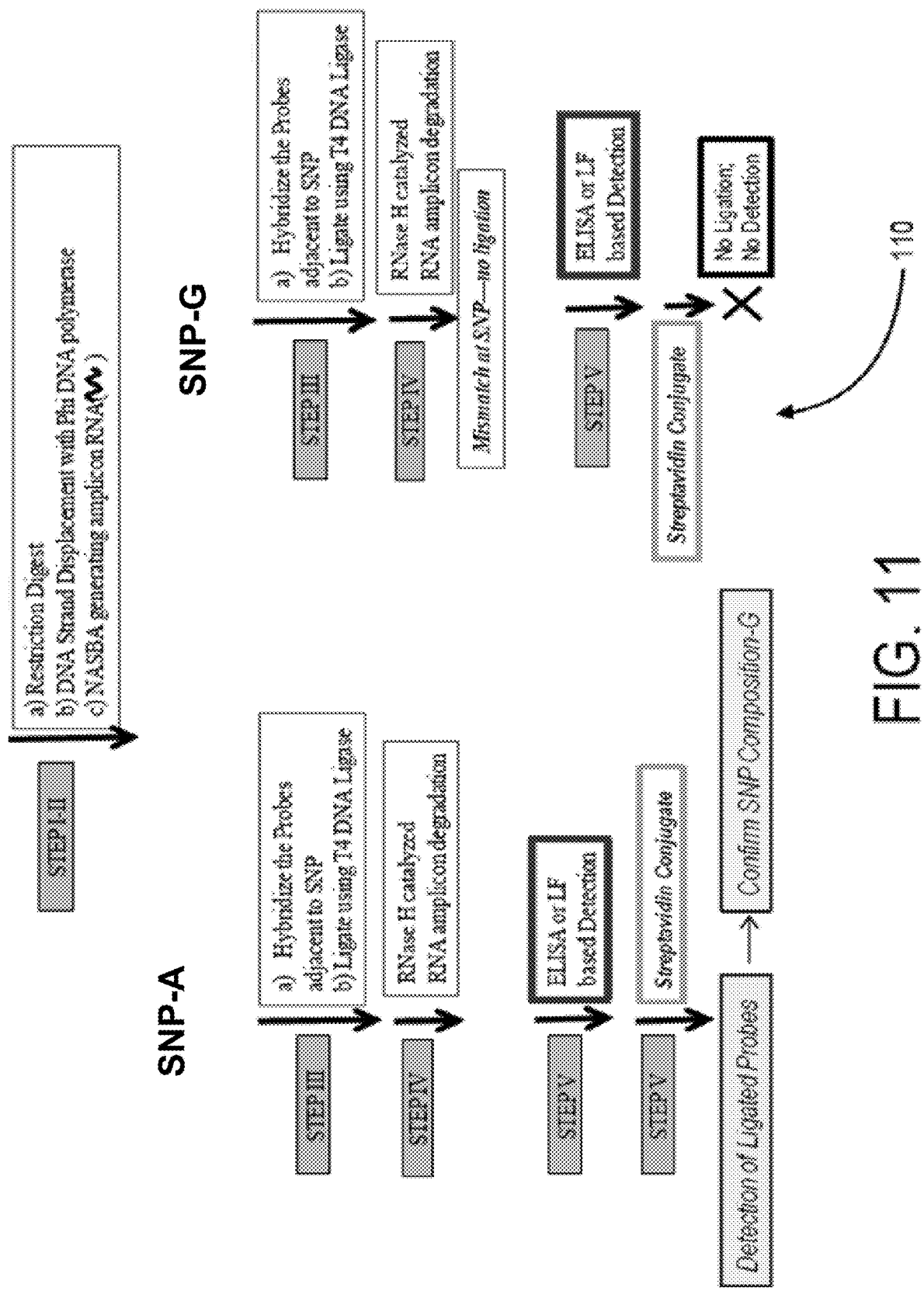
FIG. 11 illustrates a detailed overview of a method for identifying a target human individual according to an example embodiment.
Figure 12:
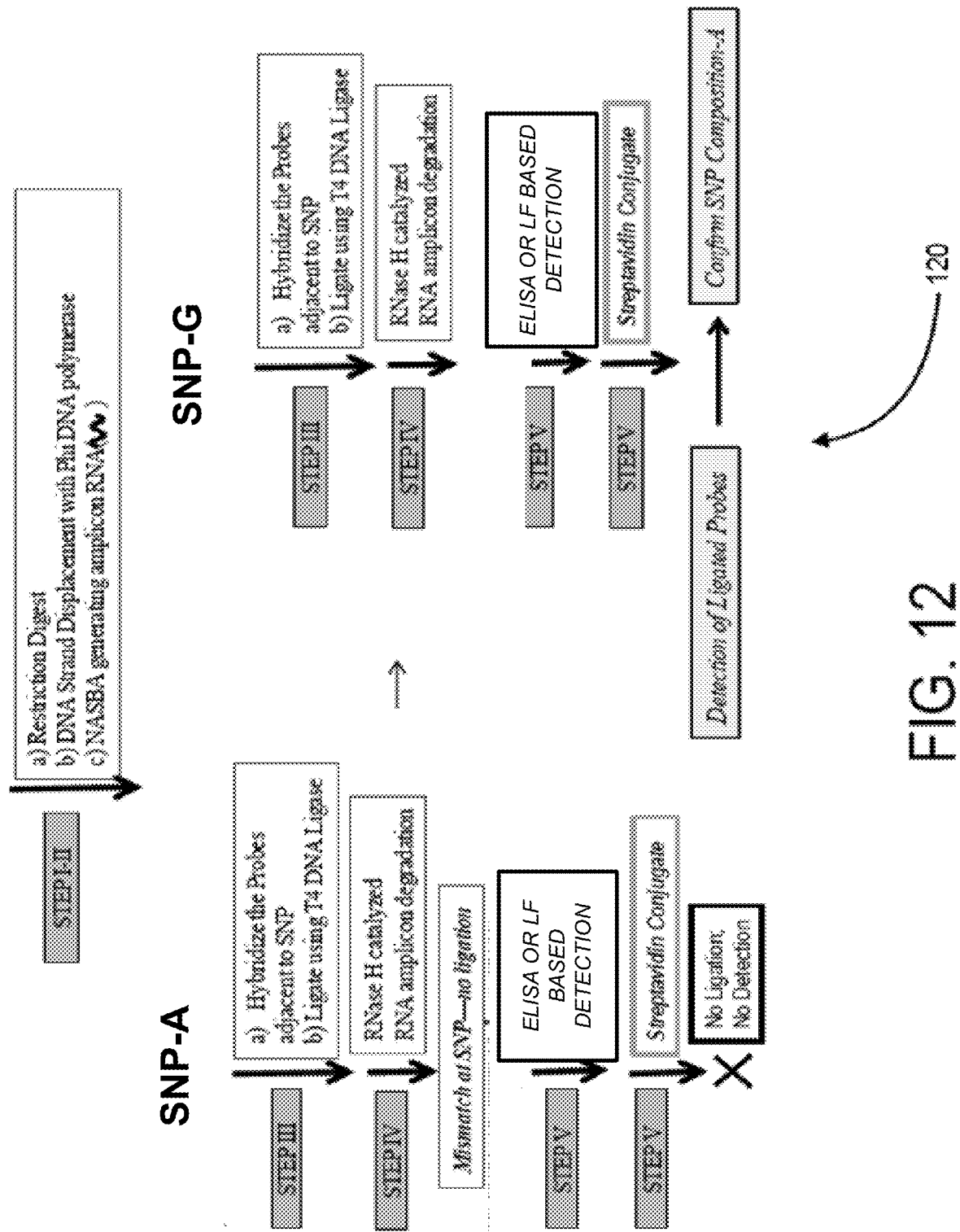
FIG. 12 illustrates a detailed overview of a method for identifying a target human individual according to an example embodiment.

FIG. 8, for instance, illustrates a block diagram of a method for identifying a target human individual including the optional steps of performing size exclusion chromatography according to an example embodiment. As shown in FIG. 8, the method includes extraction mtDNA from the sample to form extracted mtDNA at operation 800, the optional step of performing size exclusion chromatography at operation 805, cleaving the extracted mtDNA to form cleaved mtDNA segments at operation 810, hybridizing the RNA amplicon to amplification primers at operation 815, concurrently performing DNA strand displacement on the cleaved mtDNA segments at operation 820A and amplifying the cleaved mtDNA segments to form the mtDNA segment amplicon at operation 820B, the optional step of performing size exclusion chromatography at operation 825, hybridizing the capture probe to the SNP at a 5'-terminus and hybridizing the detector partner to the SNP at a 3'-terminus at operation 830, the optional step of performing size exclusion chromatography at operation 835, ligating the detector partner-nucleic acid amplicon-capture probe complex at operation 840, degrading the RNA amplicon at operation 845, the optional step of performing size exclusion chromatography at operation 850, and performing a detection assay on the detector partner-nucleic acid amplicon-capture probe complex to identify whether the target organism is present in the sample at operation 855.

FIGS. 9-12 illustrate a detailed overview of a method for identifying a target human individual according to an example embodiment. As shown in FIGS. 9-12, overviews 90, 100, 110, and 120 generally include DNA extraction, cleaving mtDNA and hybridizing primers, NASBA, tagging the SNP with capture and detector partners, RNA template directed ligation, RNase directed RNA degradation, and capture and detection of the SNP indicators.

In another aspect, certain exemplary embodiments provide a handheld device for identifying a target organism (e.g., a target human individual). According to certain embodiments, for example, the device may include a nucleic acid extraction portion (e.g., in a first well), the nucleic acid extraction portion being configured to extract nucleic acid from a sample to form extracted nucleic acid; a nucleic acid amplification portion (e.g., in a second well), the nucleic acid amplification portion being configured to amplify the extracted nucleic acid to form a nucleic acid amplicon; a tagging portion (e.g., in a third well), the tagging portion being configured to hybridize the nucleic acid amplicon to a capture probe and a detector partner to form a detector partner-nucleic acid amplicon-capture probe complex; and a detection portion (e.g., in a fifth well), the detection portion being configured to perform a detection assay on the detector partner-nucleic acid amplicon-capture probe complex.

In accordance with certain exemplary embodiments, for instance, the device may further comprise a flow buffer application portion, the flow buffer application portion being configured to add a flow buffer to the detector partner-nucleic acid amplicon-capture probe complex. In some embodiments, for example, the device may further comprise an RNA amplicon digestion portion when the target organism comprises a human individual. In further embodiments, for instance, the device may comprise at least four manual gates, one of the at least four manual gates being positioned between each of the nucleic acid extraction portion and the nucleic acid amplification portion, the nucleic acid amplification portion and the tagging portion, the tagging portion and the RNA amplicon digestion portion, and the RNA amplicon digestion portion and the detection portion. In certain embodiments, for example, the device may comprise a plurality of microfluidic channels positioned between each of the nucleic acid extraction portion and the nucleic acid amplification portion, the nucleic acid amplification portion and the tagging portion, the tagging portion and the RNA digestion portion, and the RNA digestion portion and the detection portion.

Figure 13:
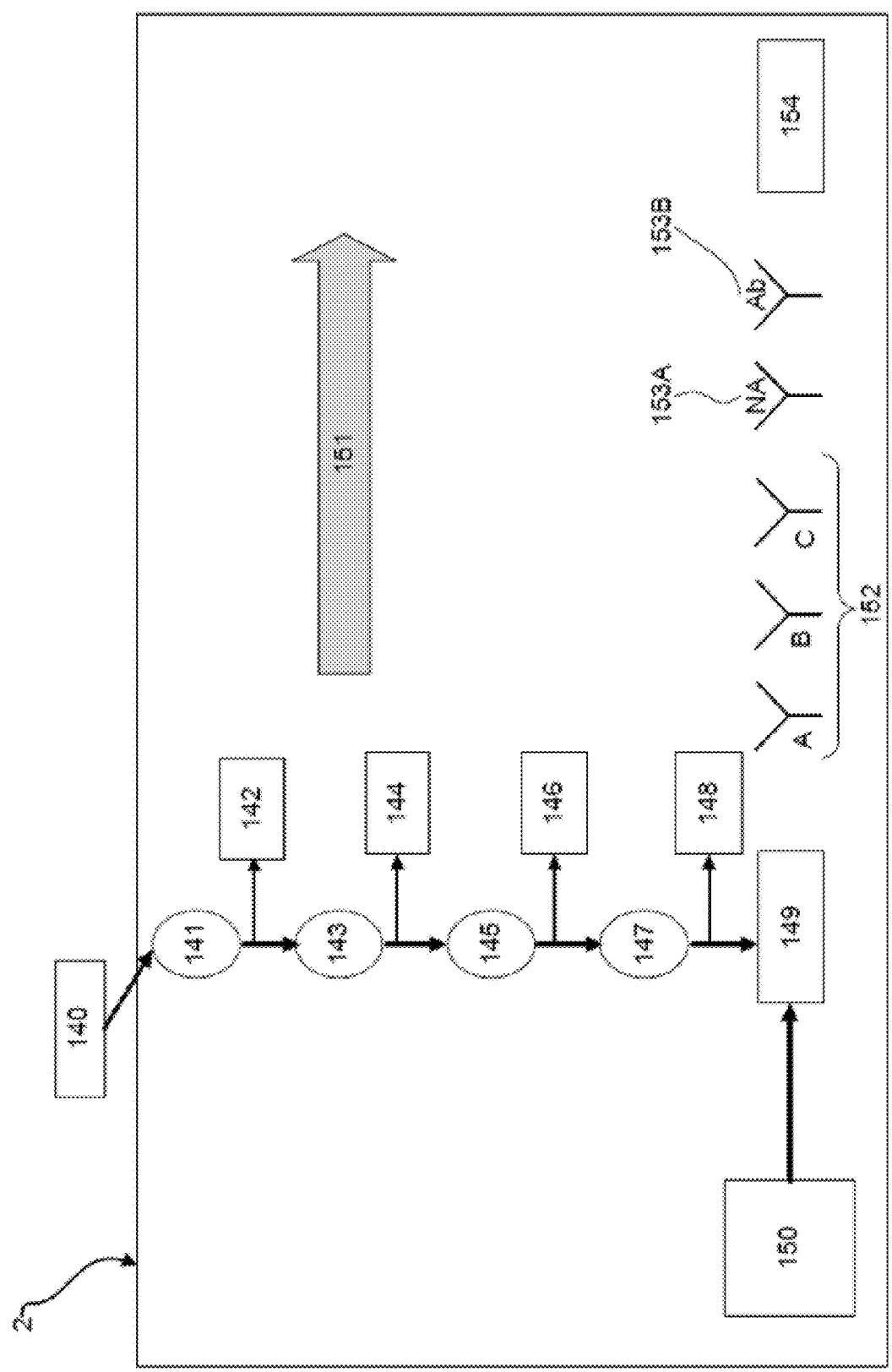
FIG. 13 illustrates a schematic for a handheld device for identifying a target human individual according to an example embodiment.

FIG. 13, for instance, illustrates a schematic for a handheld device for identifying a target human individual according to an example embodiment. As shown in FIG. 13, the device 2 includes an extraction well 141, an amplification well 143, a tagging and ligation well 145, and an RNA amplicon digestion well 147 prior to the detection assay portion. Each of the extraction well 141, amplification well 143, tagging and ligation well 145, RNA amplicon digestion well 147, and conjugate pad 149 of the detection assay are separated by manual gates 142, 144, 146, and 148 respectively, which utilize size exclusion chromatography or other selective binding to determine what molecules continue to the next well. To operate the device 2, a sample 140 is placed in the extraction well 141. After processing in the extraction well 141, the extracted nucleic acid flows through manual gate 142 and to amplification well 143. After amplification, the nucleic acid amplicon flows through manual gate 144 and to tagging and ligation well 145. After hybridizing with the capture probe and the detector partner, the detector partner-nucleic acid amplicon-capture probe complex flows through manual gate 146 and to RNA amplicon digestion well 147. After the degradation of the RNA amplicon, the complex flows through manual gate 148 and to conjugate pad 149. Flow buffer is provided from flow buffer portion 150 to push the complex through the detection assay in the flow direction 151, where the complex encounters bound antibodies 152, a nucleic acid control 153A, and an antibody control 153B before ending at the absorbent pad 154.

Figure 14:
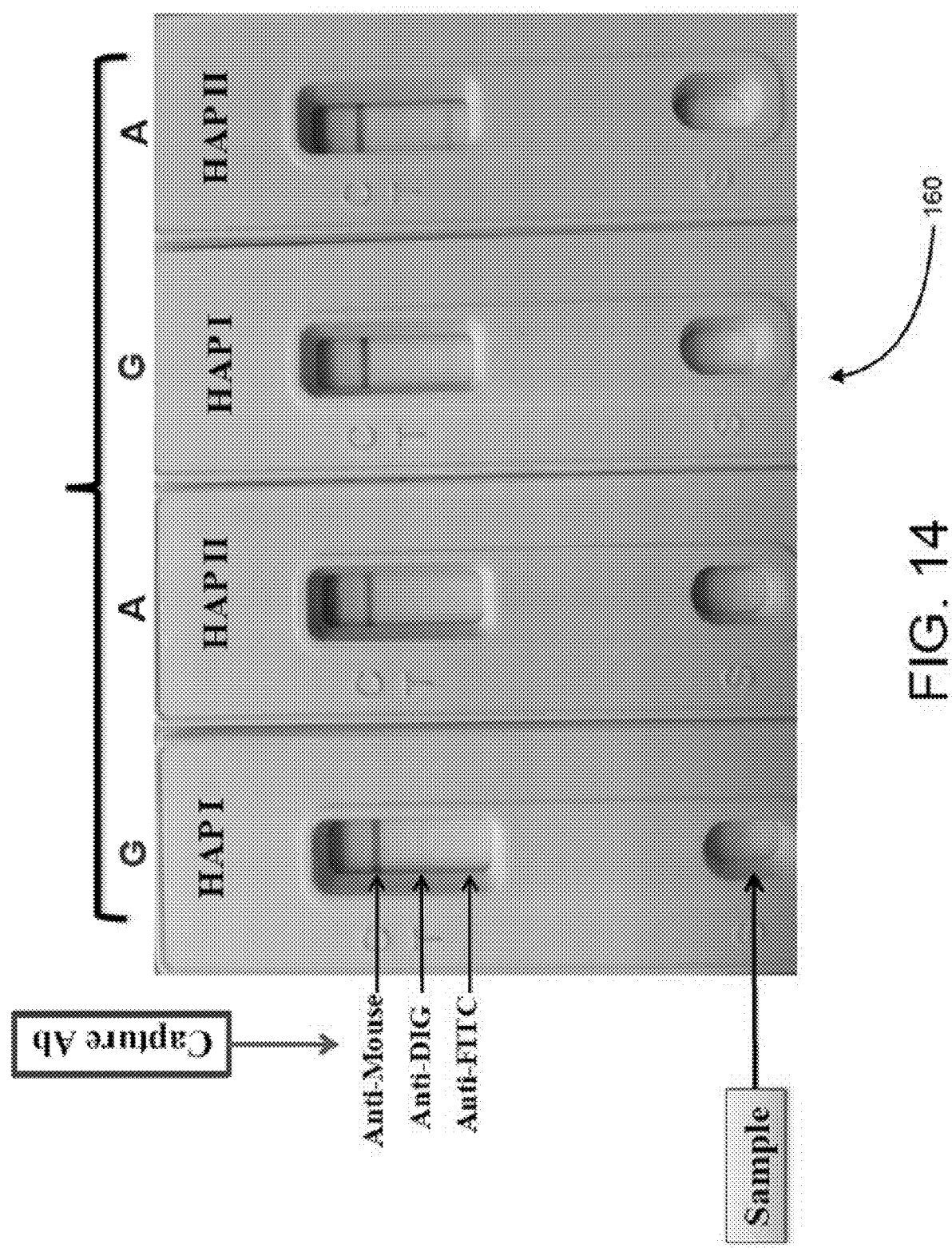
FIG. 14 illustrates a handheld device for identifying a target human individual and sample reads from a run utilizing said handheld device according to an example embodiment.

FIG. 14, for example, illustrates a handheld device for identifying a target human individual and sample reads from a run utilizing said handheld device according to an example embodiment. As shown in FIG. 14, the device 160 utilizes paper strips (e.g., much like a pregnancy test) to detect particular SNP profiles. The sample migrates up the paper strip through microfluidic channels to the detection assay portion, where the results of the test may be determined. In this regard, certain exemplary embodiments may provide a handheld platform for DNA analysis to enable the interrogation of base compositions at specific positions within mtDNA in order to extract unique SNP profiles.

Exemplary Embodiments

Certain exemplary embodiments provide methods for identifying a target organism. For instance, this method provides a lightweight, cost-effective means of identifying, for instance, pathogens and/or individuals. As such, for example, the method may permit the identification of pathogens and/or individuals at sample collection sites, thereby limiting the need to ship samples to laboratories and, as a result, providing rapid readouts, thereby permitting faster identification of pathogens and/or individuals in urgent situations (e.g., disease outbreak, criminal activity, etc.). In one aspect, the method for identifying a target organism includes extracting a nucleic acid from a sample to form an extracted nucleic acid, amplifying the extracted nucleic acid to form a nucleic acid amplicon, tagging the nucleic acid amplicon with a capture probe and a detector partner to form a detector partner-nucleic acid amplicon-capture probe complex, and performing a detection assay on the detector partner-nucleic acid amplicon-capture probe complex to identify whether the target organism is present in the sample.

In accordance with certain exemplary embodiments, the method further comprises performing size exclusion chromatography or selective binding between extracting the nucleic acid and amplifying the extracted nucleic acid, and amplifying the extracted nucleic acid and tagging the nucleic acid amplicon. In some embodiments, the method further comprises adding a flow buffer to the detector partner-nucleic acid amplicon-capture probe complex prior to performing the detection assay on the detector partner-nucleic acid amplicon-capture probe complex.

In accordance with certain exemplary embodiments, amplifying the extracted nucleic acid to form the nucleic acid amplicon comprises isothermally amplifying the extracted nucleic acid. In further embodiments, isothermally amplifying the extracted nucleic acid comprises performing nucleic acid sequence-based amplification (NASBA) on the extracted nucleic acid. According to certain embodiments, performing the detection assay on the detector partner-nucleic acid amplicon-capture probe complex comprises at least one of performing a lateral flow assay or performing an enzyme-linked immunosorbent assay (ELISA). In some embodiments, the detection assay comprises a multiplex assay.

In accordance with certain exemplary embodiments, the capture probe comprises a binding moiety. In some embodiments, the detector partner comprises a biomolecule that selectively binds to at least one of a double stranded DNA, a DNA-RNA hybrid, a single stranded RNA, or any combination thereof.

In accordance with certain exemplary embodiments, the target organism comprises a biological agent. In such embodiments, extracting the nucleic acid from the sample to form the extracted nucleic acid comprises lysing the biological agent in the sample to form a lysed biological agent, and extracting RNA from the lysed biological agent to form extracted RNA.

In accordance with certain exemplary embodiments, the target organism comprises a human individual. In such embodiments, extracting the nucleic acid from the sample to form the extracted nucleic acid comprises extracting mitochondrial DNA (mtDNA) from the sample to form extracted mtDNA. In some embodiments, the nucleic acid amplicon comprises an RNA amplicon and an mtDNA amplicon, and the method further comprises cleaving the extracted mtDNA to form cleaved mtDNA segments, hybridizing the RNA amplicon to amplification primers, and concurrently performing DNA strand displacement on the cleaved mtDNA segments and amplifying the cleaved mtDNA segments to form the mtDNA segment amplicon. In such embodiments, the mtDNA segment amplicon comprises a single nucleotide polymorphism (SNP). In further embodiments, tagging the mtDNA segment amplicon with the capture probe and the detector partner to form the detector partner-nucleic acid amplicon-capture probe complex comprises hybridizing the capture probe to the SNP at a 5'-terminus, and hybridizing the detector partner to the SNP at a 3'-terminus to form the detector partner-nucleic acid amplicon-capture probe complex. In some embodiments, the method further comprises ligating the detector partner-nucleic acid amplicon-capture probe complex, and degrading the RNA amplicon after tagging the mtDNA amplicon with the capture probe and the detector partner.

In another aspect, certain exemplary embodiments provide a handheld device for identifying a target organism. For instance, this device provides a lightweight, cost-effective means of identifying, for instance, pathogens and/or individuals. As such, for example, the device may permit the identification of pathogens and/or individuals at sample collection sites, thereby limiting the need to ship samples to laboratories and, as a result, providing rapid readouts, thereby permitting faster identification of pathogens and/or individuals in urgent situations (e.g., disease outbreak, criminal activity, etc.). According to certain embodiments, the device includes a nucleic acid extraction portion, the nucleic acid extraction portion being configured to extract nucleic acid from a sample to form extracted nucleic acid; a nucleic acid amplification portion, the nucleic acid amplification portion being configured to amplify the extracted nucleic acid to form a nucleic acid amplicon; a tagging portion, the tagging portion being configured to hybridize the nucleic acid amplicon to a capture probe and a detector partner to form a detector partner-nucleic acid amplicon-capture probe complex; and a detection portion, the detection portion being configured to perform a detection assay on the detector partner-nucleic acid amplicon-capture probe complex.

In accordance with certain exemplary embodiments, the device further comprises a flow buffer application portion, the flow buffer application portion being configured to add a flow buffer to the detector partner-nucleic acid amplicon-capture probe complex; at least three manual gates, one of the at least three manual gates being positioned between each of the nucleic acid extraction portion and the nucleic acid amplification portion, the nucleic acid amplification portion and the tagging portion, and the tagging portion and the detection portion; and a plurality of microfluidic channels positioned between each of the nucleic acid extraction portion and the nucleic acid amplification portion, the nucleic acid amplification portion and the tagging portion, and the tagging portion and the detection portion. In some embodiments, the device further comprises an RNA amplicon digestion portion when the target organism comprises a human individual. In further embodiments, the device comprises at least four manual gates, one of the at least four manual gates being positioned between each of the nucleic acid extraction portion and the nucleic acid amplification portion, the nucleic acid amplification portion and the tagging portion, the tagging portion and the RNA amplicon digestion portion, and the RNA amplicon digestion portion and the detection portion.

Gene sequences (e.g., Ebola Virus L gene, Lassa Virus GPC, Dengue Virus, and Yellow Fever Virus) and other content may be found for example in: U.S. Pat. Nos. 8,735,369; 8,124,592; 7,312,036; 8,715,694; 6,589,531; 6,171,854 and U.S. Patent Application Publication Nos. 2012/025150; 2012/0219576; 2010/0291144; 2013/0089558, the contents of which are incorporated herein by reference in their entirety.

Many modifications and other embodiments will come to mind to one skilled in the art to which this disclosure pertains having the benefit of the teachings presented in the foregoing descriptions and the associated drawings. Therefore, it is to be understood that this disclosure is not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A handheld device for identifying a predefined target organism in a sample, the device comprising:
   a nucleic acid extraction portion, the nucleic acid extraction portion being configured to extract nucleic acid from a sample to form an extracted nucleic acid;
   a nucleic acid amplification portion, the nucleic acid amplification portion being configured to amplify the extracted nucleic acid to form a nucleic acid amplicon;
   a tagging portion, the tagging portion being configured to hybridize the nucleic acid amplicon to a capture probe and a detector partner to form a detector partner-nucleic acid amplicon-capture probe complex, the detector partner comprising an antibody labeled with a detector moiety; and
   a detection portion, the detection portion being configured to perform a detection assay on the detector partner-nucleic acid amplicon-capture probe complex to identify whether the predefined target organism is present in the sample.

2. The device of claim 1, further comprising:
   a flow buffer application portion, the flow buffer application portion being configured to add a flow buffer to the detector partner-nucleic acid amplicon-capture probe complex;
   at least three manual gates, one of the at least three manual gates being positioned between the nucleic acid extraction portion and the nucleic acid amplification portion or between the nucleic acid amplification portion and the tagging portion or between the tagging portion and the detection portion; and
   a plurality of microfluidic channels positioned among the nucleic acid extraction portion, the nucleic acid amplification portion, the nucleic acid amplification portion, the tagging portion, the tagging portion and the detection portion.

3. The device of claim 1, further comprising an RNA amplicon digestion portion when the predefined target organism is from a human individual.

4. The device of claim 3, wherein the device comprises at least four manual gates, one of the at least four manual gates being positioned between the nucleic acid extraction portion and the nucleic acid amplification portion or between the nucleic acid amplification portion and the tagging portion or between the tagging portion and the RNA amplicon digestion portion or between the RNA amplicon digestion portion and the detection portion.

5. The device of claim 1, wherein said being configured to amplify the extracted nucleic acid is by isothermally amplifying the extracted nucleic acid.

6. The device of claim 5, wherein said isothermally amplifying the extracted nucleic acid comprises performing nucleic acid sequence-based amplification (NASBA) on the extracted nucleic acid.

7. The device of claim 1, wherein the detection portion is further configured to perform at least one of a lateral flow assay and an enzyme-linked immunosorbent assay (ELISA).

8. The device of claim 1, wherein the detection assay comprises a multiplex assay.

9. The device of claim 1, wherein the capture probe comprises a binding moiety.

10. The device of claim 1, wherein the detector moiety comprises a gold nanoparticle.

11. The device of claim 1, wherein the predefined target organism comprises a biological agent.

12. The device of claim 11, wherein the nucleic acid extraction portion is further configured to:
   lyse the biological agent in the sample to form a lysed biological agent; and
   extract RNA from the lysed biological agent to form an extracted RNA.

13. The device of claim 1, wherein the predefined target organism is from a human individual.

14. The device of claim 13, wherein the nucleic acid extraction portion is further configured to extract mitochondrial DNA (mtDNA) from the sample to form an extracted mtDNA.

15. The device of claim 14, wherein the nucleic acid amplicon comprises an RNA amplicon and an mtDNA amplicon when the extracted nucleic acid contains RNAs and the mtDNA, the device further configured to:
- cleave the extracted mtDNA to form cleaved mtDNA segments;
- hybridize the RNA amplicon to amplification primers; and
- concurrently perform DNA strand displacement on the cleaved mtDNA segments and amplify the cleaved mtDNA segments to form a mtDNA segment amplicon, wherein the mtDNA segment amplicon comprises a single nucleotide polymorphism (SNP).

16. The device of claim 15, wherein the nucleic acid amplicon of the detector partner-nucleic acid amplicon-capture probe complex is the mtDNA segment amplicon, the capture probe of the detector partner-nucleic acid amplicon-capture probe complex hybridizes to the SNP when the SNP is located at a 5'-terminus of the mtDNA segment amplicon, and the detector partner of the detector partner-nucleic acid amplicon-capture probe complex hybridizes to the SNP when the SNP is located at 3'-terminus of the mtDNA segment amplicon.

17. The device of claim 16, wherein the capture probe and the detector partner in the detector partner-nucleic acid amplicon-capture probe complex is ligated, and the RNA amplicon is degraded after hybridizing the mtDNA amplicon with the capture probe and the detector partner.

* * * * *